(12) United States Patent
Anchang et al.

(10) Patent No.: US 10,436,771 B2
(45) Date of Patent: Oct. 8, 2019

(54) SYSTEMS AND METHODS FOR TARGETED THERAPY BASED ON SINGLE-CELL STIMULUS PERTURBATION RESPONSE

(71) Applicant: The Board of Trustees of the Leland Stanford Junior University, Stanford, CA (US)

(72) Inventors: Benedict Anchang, Stanford, CA (US); Sylvia K. Plevritis, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 38 days.

(21) Appl. No.: 15/480,327

(22) Filed: Apr. 5, 2017

(65) Prior Publication Data

US 2017/0285004 A1    Oct. 5, 2017

Related U.S. Application Data

(60) Provisional application No. 62/318,609, filed on Apr. 5, 2016, provisional application No. 62/481,540, filed on Apr. 4, 2017.

(51) Int. Cl.
   *G01N 33/50* (2006.01)
   *G06F 19/26* (2011.01)
   (Continued)

(52) U.S. Cl.
   CPC ... *G01N 33/5011* (2013.01); *G01N 33/56966* (2013.01); *G01N 33/6848* (2013.01);
   (Continued)

(58) Field of Classification Search
   CPC .......... G01N 33/5011; G01N 33/5041; G01N 33/56966; G01N 33/6848; G01N 33/6851;
   (Continued)

(56) References Cited

U.S. PATENT DOCUMENTS

2011/0059861 A1* 3/2011 Nolan ............... G01N 33/5091
                                                                506/10
2013/0071860 A1* 3/2013 Hale .................... C12Q 1/6883
                                                                435/7.24

(Continued)

FOREIGN PATENT DOCUMENTS

EP       3440580 A1    2/2019
WO   2017176946 A1   10/2017

OTHER PUBLICATIONS

Anchang, Benedict et al. "Abstract B1-39: Multi-target drug combinations from single drug responses measured at the level of single cells using Mixture Nested Effects Models (MNEMs) applied to cancer." Cancer Research (2015) vol. 75, Issue 22, Supplement 2. (Year: 2015).*

(Continued)

*Primary Examiner* — Christopher Adam Hixson
(74) *Attorney, Agent, or Firm* — KPPB LLP

(57) ABSTRACT

Systems and methods for targeted therapy based on single-cell stimulus perturbation response. In one embodiment, a method for optimizing stimulus combinations for therapy includes receiving a cell sample, treating the cell sample with a plurality of stimuli by treating a different portion of the cell sample with one of the plurality of stimuli for each of the plurality of stimuli, labeling the cell sample with a plurality of metal-conjugated probes, analyzing the cell sample using a mass spectrometer, obtaining mass spectrometry data from the mass spectrometer, identifying subpopulations within the cell sample using the mass spectrometry data, computing stimulus effects, generating a nested-effects model using the mass spectrometry data, and scoring stimuli combinations using the computing device, wherein the stimulus combinations are combinations made from the plurality of stimuli.

10 Claims, 31 Drawing Sheets

(51) Int. Cl.
G01N 33/68 (2006.01)
G06F 19/12 (2011.01)
G16B 5/00 (2019.01)
G16B 45/00 (2019.01)
G01N 33/569 (2006.01)
G16H 10/40 (2018.01)
G06F 19/00 (2018.01)

(52) U.S. Cl.
CPC .............. *G16B 5/00* (2019.02); *G16B 45/00* (2019.02); *G16H 10/40* (2018.01); *G06F 19/325* (2013.01)

(58) Field of Classification Search
CPC .......... G06F 19/12; G06F 19/18; G06F 19/24; G06F 19/26; G06F 19/325
See application file for complete search history.

(56) References Cited

U.S. PATENT DOCUMENTS

| | | | |
|---|---|---|---|
| 2014/0329272 A1 | 11/2014 | Bodenmiller et al. | |
| 2015/0287578 A1 | 10/2015 | Bendall et al. | |
| 2015/0345047 A1* | 12/2015 | Sander | C40B 30/02 506/8 |

OTHER PUBLICATIONS

International Preliminary Report on Patentability for International Application PCT/US2017/026243, Report dated Oct. 9, 2018, dated Oct. 18, 2018, 7 Pgs.
International Search Report and Written Opinion for International Application No. PCT/US2017/026243, Search completed Jun. 12, 2015, dated Jun. 26, 2017, 13 Pgs.
Adachi et al., "The Human Pre-B Cell Line Nalm-6 Is Highly Proficient in Gene Targeting by Homologous Recombination", DNA and Cell Biology, vol. 25, No. 1, Jan. 11, 2006, pp. 19-24.
Amir et al., "viSNE enables visualization of high dimensional single-cell data and reveals phenotypic heterogeneity of leukemia", Nature Biotechnology, vol. 31, May 19, 2013, pp. 545-552.
Anchang et al., "CCAST: A Model-Based Gating Strategy to Isolate Homogeneous Subpopulations in a Heterogeneous Population of Single Cells", PLoS Computational Biology, vol. 10, No. 7, Jul. 31, 2014, 14 pgs.
Anchang et al., "Modeling the Temporal Interplay of Molecular Signaling and Gene Expression by Using Dynamic Nested Effects Models", Proceedings of the National Academy of Sciences of the United States of America, vol. 106, No. 16, Apr. 21, 2009, pp. 6447-6452.
Anchang et al., "Visualization and cellular hierarchy inference of single-cell data using Spade", Nature Protocols, vol. 11, No. 7, 2016, Published online Jun. 16, 2016, pp. 1264-1279, 2016.
Artimo et al., "ExPASy: SIB bioinformatics resource portal", Nucleic Acids Research, vol. 40, No. W1, Jul. 2012, Electronic Publication: May 31, 2012, pp. W597-W603.
Ashkenazi et al., "Death Receptors: Signaling and Modulation", Science, vol. 281, No. 5381, Aug. 28, 1998, pp. 1305-1308.
Bagheri et al., "A Dynamical Systems Model for Combinatorial Cancer Therapy Enhances Oncolytic Adenovirus Efficacy by MEK-Inhibition", PLoS Computational Biology, vol. 7, No. 2, Feb. 17, 2011, 10 pgs.
Bendall et al., "Single-Cell Mass Cytometry of Differential Immune and Drug Responses Across a Human Hematopoietic Continuum", Science, May 6, 2011, vol. 332, No. 6030, pp. 687-696.
Bodenmiller et al., "Multiplexed mass cytometry profiling of cellular states perturbed by small-molecule regulators", Nature Biotechnology, vol. 30, No. 9, Aug. 19, 2012, pp. 858-867.
Dyer et al., "Barriers to Effective TRAIL-Targeted Therapy of Malignancy", Journal of Clinical Oncology, vol. 25, No. 28, Oct. 1, 2007, pp. 4505-4506.
Einsiedel et al., "Long-Term Outcome in Children With Relapsed ALL by Risk-Stratified Salvage Therapy: Results of Trial Acute Lymphoblastic Leukemia-Relapse Study of the Berlin-Frankfurt-Munster Group 87", Journal of Clinical Oncology, vol. 23, No. 31, Nov. 1, 2005, pp. 7942-7950.
Falschlehner et al., "TRAIL signalling: Decisions between life and death", The International Journal of Biochemistry & Cell Biology, vol. 39, No. 7-8, Jul.-Aug. 2007, pp. 1462-1475.
Frohlich et al., "Analyzing gene perturbation screens with nested effects models in R and bioconductor", Bioinformatics, vol. 24, No. 21, Nov. 1, 2008, pp. 2549-2550.
Frohlich et al., "Estimating large-scale signaling networks through nested effect models with intervention effects from microarray data", Bioinformatics, vol. 24, No. 22, Nov. 15, 2008, pp. 2650-2656.
Frohlich et al., "Fast and efficient dynamic nested effects models", Bioinformatics, vol. 27, No. 2, Jan. 15, 2011, pp. 238-244.
Harned et al., "Relapsed Acute Lymphoblastic Leukemia: Current Status and Future Opportunities", Current Oncology Reports, vol. 10, No. 6, Nov. 2008, pp. 453-458.
Howlader et al., "Childhood Cancer by the ICCC", National Cancer Institute: Surveillance, Epidemiology, and End Results Program, SEER Cancer Statistics Review, 1975-2013, Bethesda, MD, Apr. 8, 2015, 11 pgs.
Jacob et al., "Detecting hierarchical structure in molecular characteristics of disease using transitive approximations of directed graphs", Bioinformatics, vol. 24, No. 7, Apr. 1, 2008, pp. 995-1001.
Janes et al., "Effective and selective targeting of leukemia cells using a TORC1/2 kinase inhibitor", Nature Medicine, vol. 16, Jan. 13, 2010, pp. 205-213.
Koschny et al., "The promise of TRAIL—potential and risks of a novel anticancer therapy", Journal of Molecular Medicine, vol. 85, No. 9, Sep. 2007, pp. 923-935.
Krishnaswamy et al., "Conditional density-based analysis of T cell signaling in single-cell data", Science, vol. 346, No. 6213, Nov. 28, 2014, 17 pgs.
Lackner et al., "Mechanisms of acquired resistance to targeted cancer therapies", Future Oncology, vol. 8, No. 8, Aug. 15, 2012, pp. 999-1014.
Lee et al., "Sequential Application of Anticancer Drugs Enhances Cell Death by Rewiring Apoptotic Signaling Networks", Cell, vol. 149, No. 4, May 11, 2012, pp. 780-794.
Li et al., "Network target for screening synergistic drug combinations with application to traditional Chinese medicine", BMC Systems Biology, vol. 5, Supp. 1, Jun. 20, 2011, 13 pgs.
Lim et al., "p38MAPK inhibitor SB203580 sensitizes human SNU-C4 colon cancer cells to exisulind-induced apoptosis", Oncology Reports, vol. 16, No. 5, Nov. 2006, pp. 1131-1135.
Lo et al., "flowClust: a Bioconductor package for automated gating of flow cytometry data", BMC Bioinformatics, vol. 10, No. 145, May 14, 2009, 8 pgs.
Markowetz, "How to Understand the Cell by Breaking It: Network Analysis of Gene Perturbation Screens", PLoS Computational Biology., vol. 6, No. 2, e1000655; p. 1, 3rd column, 2nd paragraph; p. 4, 1st column, 1st paragraph; p. 4, 1st column 3rd paragraph; p. 4, 2nd column, 1st paragraph p. 4, 3rd column, 2nd paragraph; Figure 3, DOI: 10.1371/journal.pcbi.1000655, Feb. 26, 2010, pp. 1-8.
Markowetz et al., "Nested effects models for high-dimensional phenotyping screens", Bioinformatics, vol. 23, No. 13, Jul. 1, 2007, pp. i305-i312.
Markowetz et al., "Non-transcriptional pathway features reconstructed from secondary effects of RNA interference", Bioinformatics, vol. 21, No. 21, Sep. 13, 2005, pp. 4026-4032.
Michor et al., "The Origins and Implications of Intratumor Heterogeneity", Cancer Prevention Research, vol. 3, No. 11, Nov. 2010, pp. 1361-1364.
Minowada et al., "A Non-T, Non-B Human Leukemia Cell Line (NALM-1): Establishment of the Cell Line and Presence of Leukemia-Associated Antigens", JNCI: Journal of the National Cancer Institute, vol. 59, No. 1, Jul. 1977, pp. 83-87.

(56) References Cited

OTHER PUBLICATIONS

Naumovski et al., "Philadelphia Chromosome-positive Acute Lymphoblastic Leukemia Cell Lines without Classical Breakpoint Cluster Region Rearrangement", Cancer Research, vol. 48, No. 10, May 15, 1988, pp. 2876-2879.

Niederberger et al., "MC EMiNEM Maps the Interaction Landscape of the Mediator", PLoS Computational Biology, vol. 8, No. 6, Jun. 21, 2012, 10 pgs.

Pirkl et al., "Analyzing synergistic and non-synergistic interactions in signalling pathways using Boolean Nested Effect Models", Bioinformatics, vol. 32, No. 6, Mar. 15, 2016, pp. 893-900.

Pyne et al., "Automated High-Dimensional Flow Cytometric Data Analysis", PNAS, May 26, 2009, vol. 106, No. 21, pp. 8519-8524.

Qiu et al., "Extracting a cellular hierarchy from high-dimensional cytometry data with SPADE", Nature Biotechnology, vol. 29, No. 10, Oct. 2011, Published online Oct. 2, 2011, pp. 886-893.

Ryall et al., "Systems biology approaches for advancing the discovery of effective drug combinations", Journal of Cheminformatics, vol. 7, No. 7, Feb. 26, 2015, 15 pgs.

Salama et al., "Trametinib (GSK1120212) in the treatment of melanoma", Expert Opinion on Pharmacotherapy, vol. 14, No. 5, Feb. 23, 2013, pp. 619-627.

Shekhar et al., "Automatic Classification of Cellular Expression by Nonlinear Stochastic Embedding (ACCENSE)", Proceedings of the National Academy of Sciences of the United States of America, vol. 111, No. 1, Jan. 7, 2014, pp. 202-207.

Smyth, "Linear Models and Empirical Bayes Methods for Assessing Differential Expression in Microarray Experiments", Statistical Applications in Genetics and Molecular Biology, vol. 3, No. 1, Feb. 12, 2004, 25 pgs.

Thomas et al., "Treatment of Philadelphia chromosome-positive acute lymphocytic leukemia with hyper-CVAD and imatinib mesylate", Blood, vol. 103, No. 12, Jun. 15, 2004, pp. 4396-4407.

Tresch et al., "Structure learning in Nested Effects Models", Statistical Applications in Genetics and Molecular Biology, vol. 7, No. 1, Mar. 1, 2008, 28 pgs.

Vaske et al., "A Factor Graph Nested Effects Model to Identify Networks from Genetic Perturbations", PLoS Computational Biology, vol. 5, No. 1, Jan. 30, 2009, 16 pgs.

Wang et al., "TRAIL and apoptosis induction by TNF-family death receptors", Oncogene, vol. 22, Nov. 24, 2003, pp. 8628-8633.

Willis et al., "Life in the balance: how BH3-only proteins induce apoptosis", Current Opinion in Cell Biology, vol. 17, No. 6, Dec. 2005, pp. 617-625.

Zare et al., "Data reduction for spectral clustering to analyze high throughput flow cytometry data", BMC Bioinformatics, 2010, vol. 11, No. 403, pp. 1-16.

Zhang et al., "Mechanisms of resistance to TRAIL-induced apoptosis in cancer", Cancer Gene Therapy, vol. 12, Nov. 19, 2004, pp. 228-237.

Zhao et al., "Addressing Genetic Tumor Heterogeneity through Computationally Predictive Combination Therapy", Cancer Discovery, vol. 4, No. 2, Feb. 2014, pp. 166-174.

Zou et al., "Neighbor communities in drug combination networks characterize synergistic effect", Molecular BioSystems, vol. 8, No. 12, Sep. 5, 2012, pp. 3185-3196.

* cited by examiner

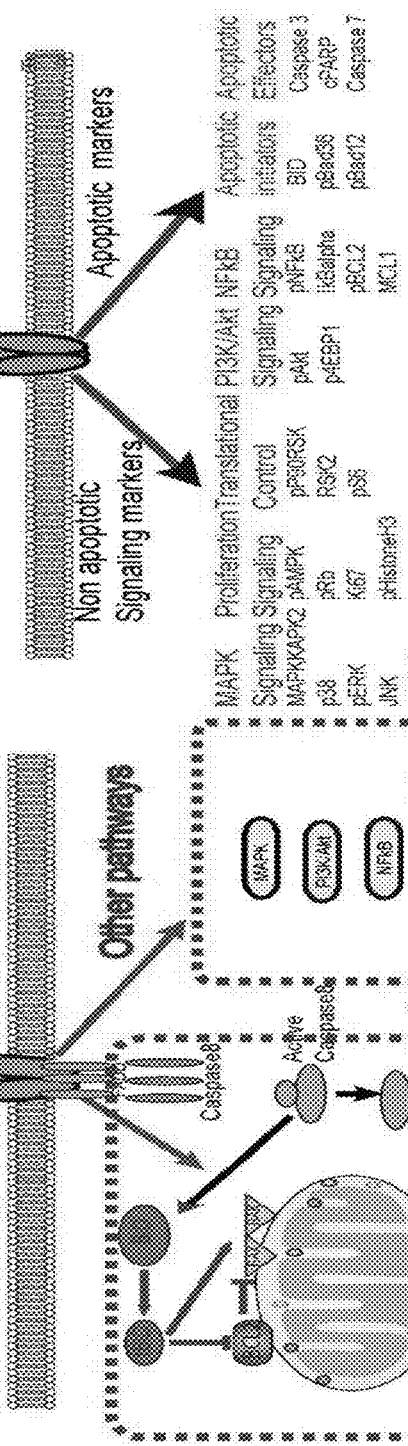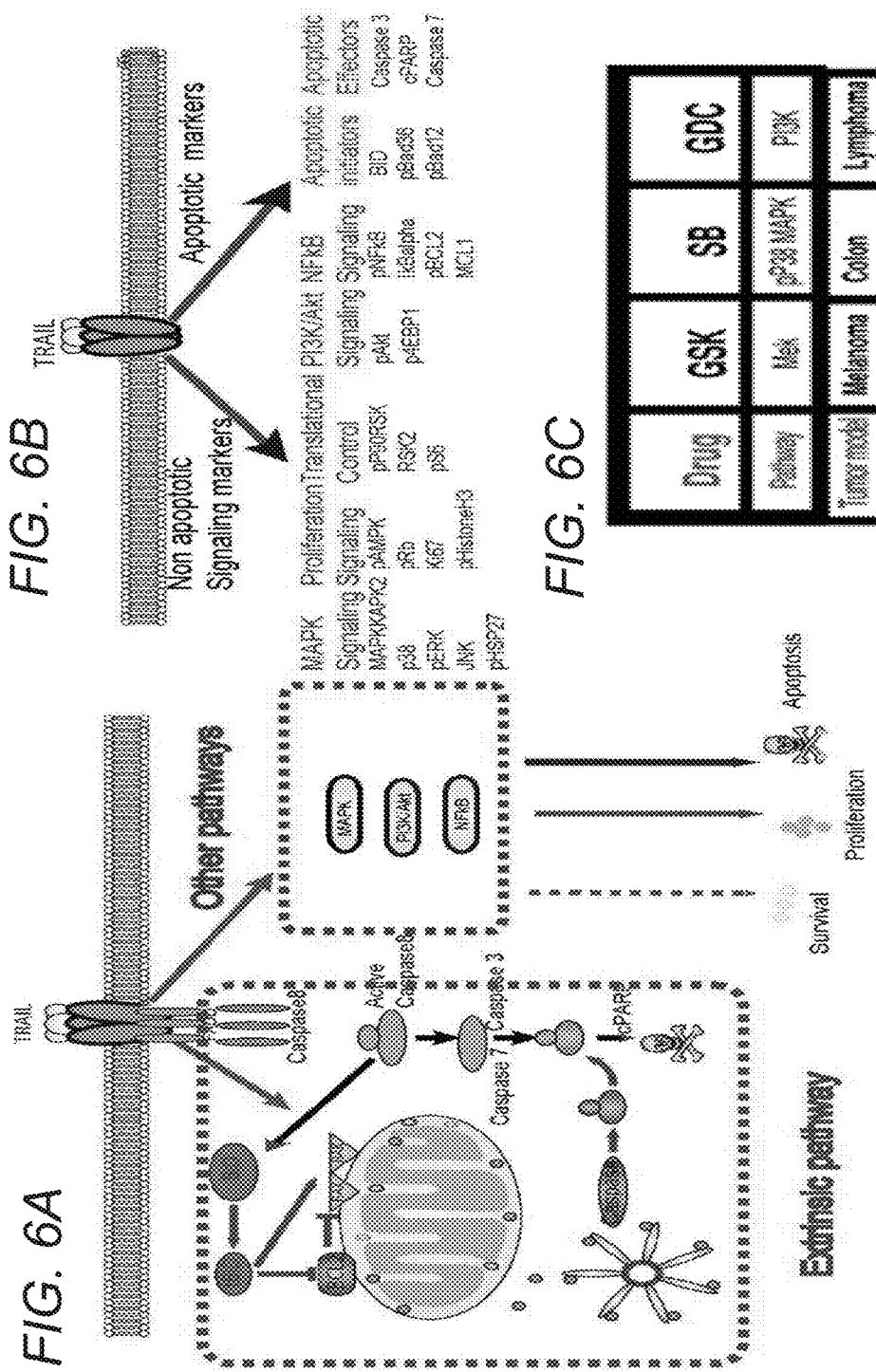

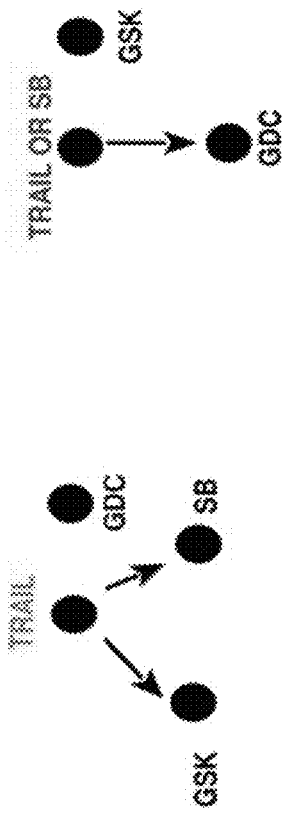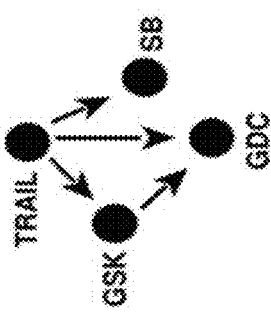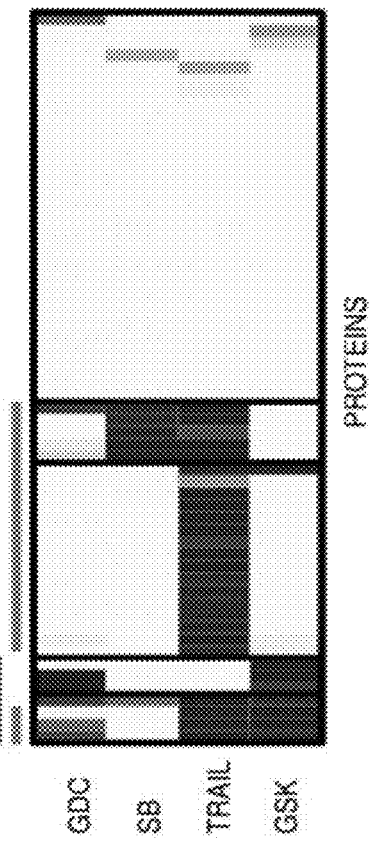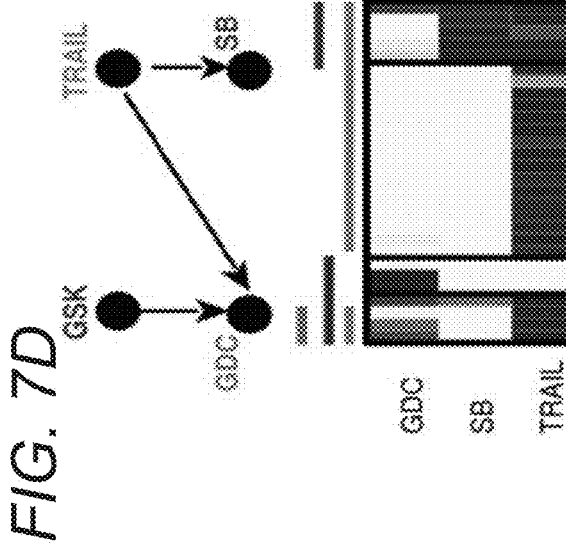
FIG. 7C  FIG. 7D  FIG. 7E

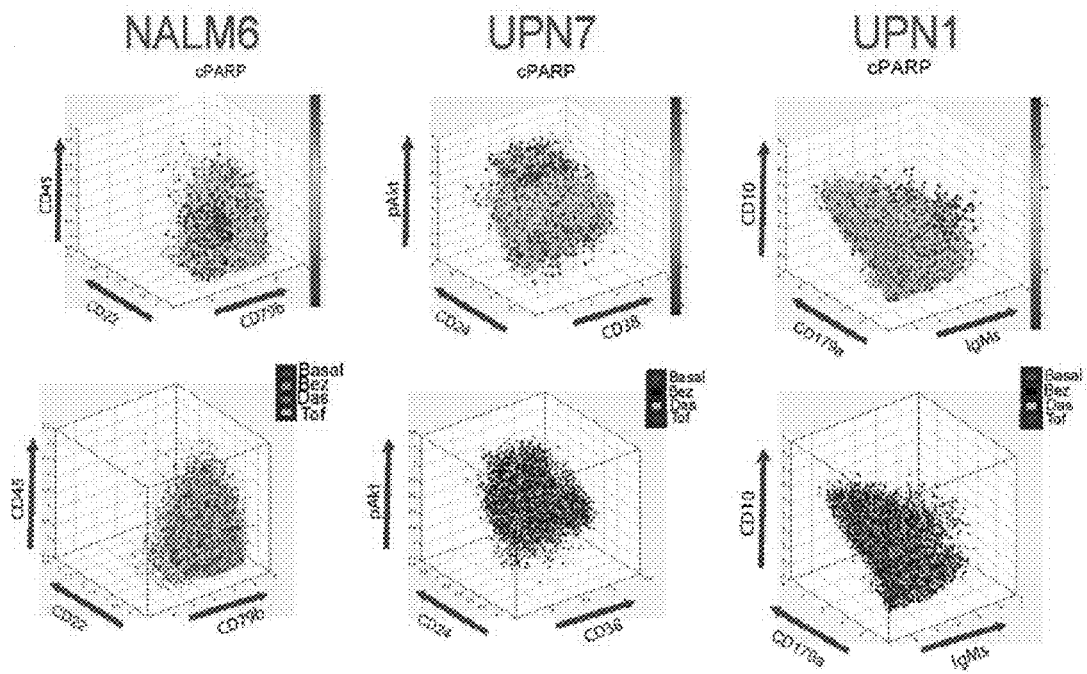

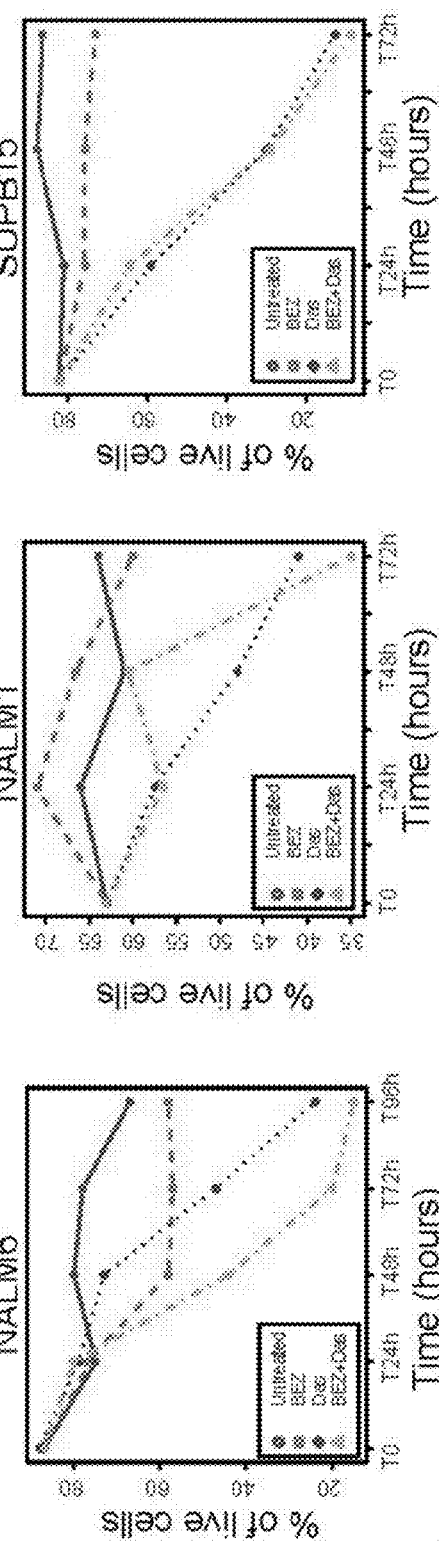
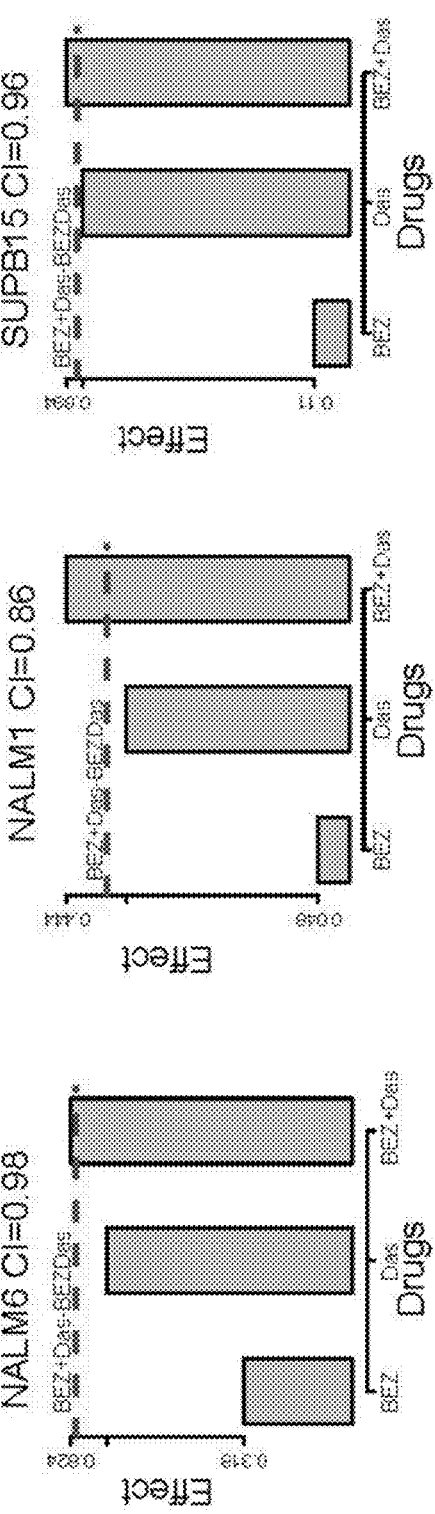
FIG. 13A
FIG. 13B

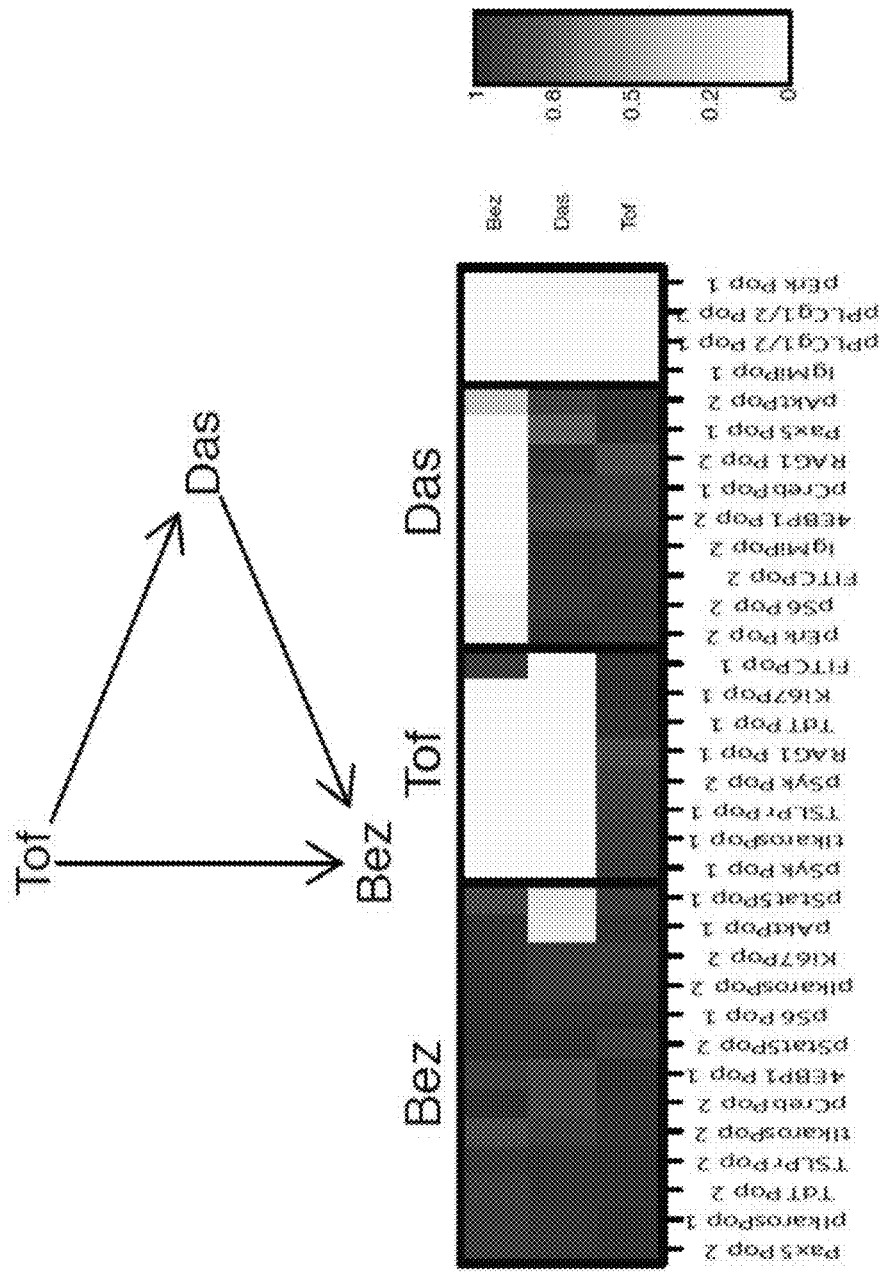
FIG. 14B Homogeneous Desired Effect Analysis

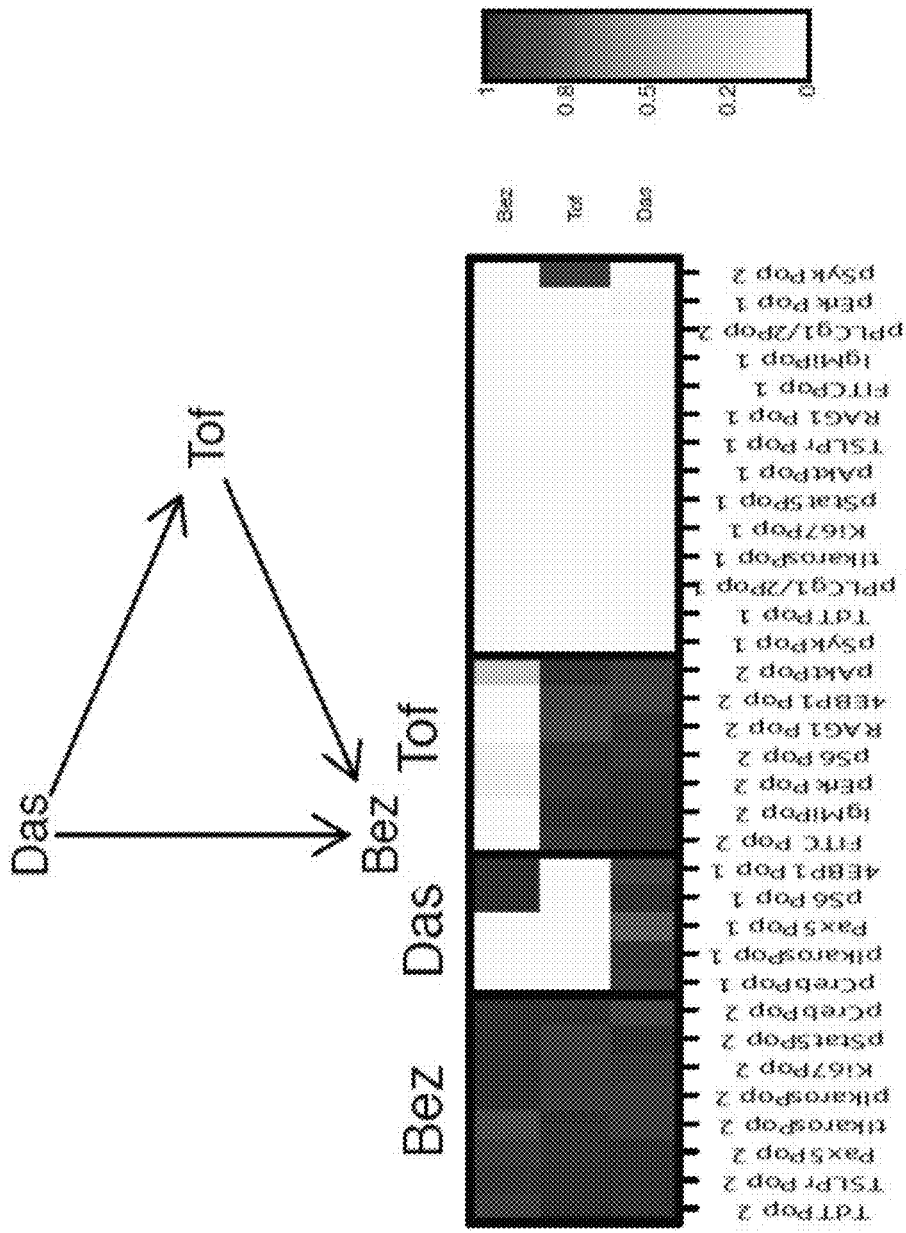
FIG. 14C Non-homogeneous Desired Effect Analysis

| DRUGNEM Ranking | |
|---|---|
| Das | 17.9681 |
| Bez Das | 17.9681 |
| Das Tof | 17.9681 |
| Tof | 13.4927 |
| Bez Tof | 13.4927 |
| Bez | 7.5958 |

FIG. 14D

SYSTEMS AND METHODS FOR TARGETED THERAPY BASED ON SINGLE-CELL STIMULUS PERTURBATION RESPONSE

CROSS-REFERENCE TO RELATED APPLICATIONS

The current application claims the benefit of and priority under 35 U.S.C. § 119(e) to U.S. Provisional Patent Application No. 62/318,609 entitled "Method for Selecting Optimal Cancer Treatment Combinations Based on Single-Cell Data Derived from a Patient Sample" to Anchang et al., filed Apr. 5, 2016 and U.S. Provisional Patent Application No. 62/481,540 entitled Personalized Cancer Therapy With Single Cell Analysis of Heterogeneous Tumors" to Anchang et al., filed Apr. 4, 2017. The disclosures of U.S. Provisional Patent Application Nos. 62/318,609 and 62/481,540 are hereby incorporated by reference in their entirety for all purposes.

STATEMENT REGARDING FEDERALLY SPONSORED RESEARCH OR DEVELOPMENT

This invention was made with Government support under contract CA149145 awarded by the National Institutes of Health. The Government has certain rights in the invention.

FIELD OF THE INVENTION

The present invention generally relates to generating targeted therapies and, more specifically, optimized stimulus combination strategies.

BACKGROUND

An individual malignant tumor is composed of a heterogeneous collection of single cells with distinct molecular and phenotypic features, a phenomenon termed intratumoral heterogeneity. Intratumoral heterogeneity is increasingly being recognized as a critical barrier to overcome stimulus resistance. Combination stimulus therapy is a treatment option that promises to improve cancer treatment by targeting multiple signaling and regulatory pathways maintaining tumor progression. This type of stimulus regimen is predicated on the concept that stimulus resistance to monotherapy is largely attributed to intratumoral heterogeneity. Therefore, it is important to take into account a targeted tumor's intratumoral heterogeneity when developing a combination stimulus regimen for the targeted tumor. Furthermore, as the number of potential FDA approved drugs increases, systematic approaches to identify combination strategies that account for this level of heterogeneity become imperative.

SUMMARY OF THE INVENTION

A method for optimizing stimulus combinations for therapy, the method including receiving a cell sample, treating the cell sample with a plurality of stimuli by treating a different portion of the cell sample with one of the plurality of stimuli for each of the plurality of stimuli, labeling the cell sample with a plurality of metal-conjugated probes, wherein the plurality of metal-conjugated probes corresponds with a set of markers, analyzing the cell sample using a mass spectrometer, obtaining mass spectrometry data from the mass spectrometer, wherein the mass spectrometry data describe perturbation responses, identifying subpopulations within the cell sample using the mass spectrometry data using a computing device, computing stimulus effects using the computing device, generating a nested-effects model using the mass spectrometry data using the computing device, wherein the nested-effects model represent the relationships between the plurality of stimuli and the set of markers across the subpopulations, and scoring stimuli combinations using the computing device, wherein the stimulus combinations are combinations made from the plurality of stimuli.

BRIEF DESCRIPTION OF THE DRAWINGS

The description and claims will be more fully understood with reference to the following figures, which are presented as exemplary embodiments of the invention and should not be construed as a complete recitation of the scope of the invention.

FIGS. 6A-6D illustrate an analysis performed on HeLa cells undergoing a panel of single stimulus candidates in accordance with an embodiment of the invention.

FIGS. 7A-7G illustrate single-cell perturbation data of HeLa cells in accordance with an embodiment of the invention.

FIGS. 8A-8G illustrate an in-vitro stimulus perturbation analysis performed at the single cell level on the NALM6 cell line and two B-cell precursor Philadelphia chromosome positive Ph+ALL pediatric patient samples in accordance with an embodiment of the invention.

FIG. 13A illustrates survival curves for three cell lines exposed to both single and stimulus combinations.

FIG. 13B illustrates a quantification of the synergistic effect of a stimulus combination across three cell lines.

FIG. 14A-14D conceptually illustrates optimizing stimulus combinations based on desired intracellular effects in accordance with an embodiment of the invention.

DETAILED DESCRIPTION

Figure 1:
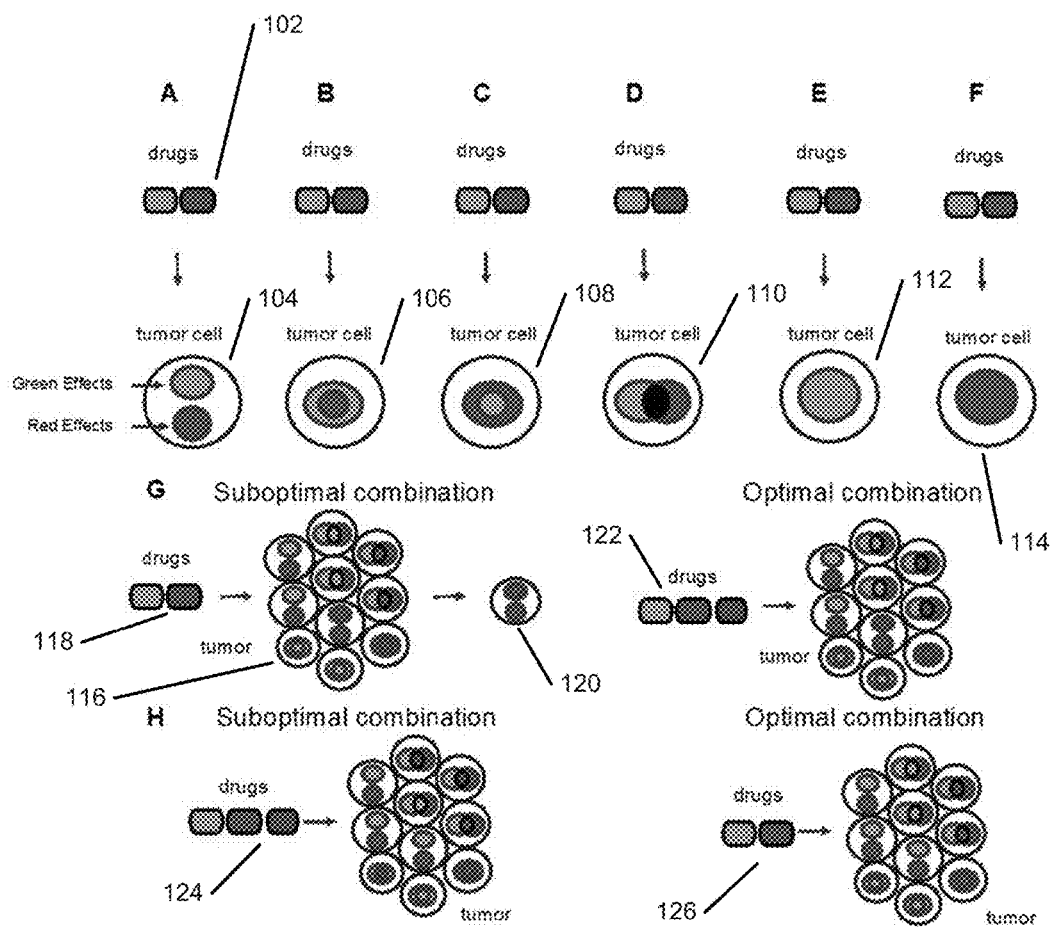
FIG. 1 conceptually illustrates stimuli combination optimization principles in accordance with an embodiment of the invention.

Turning now to the drawings, systems and methods for selecting optimal stimulus combinations that account for intratumoral heterogeneity in the tumors of specific patients are disclosed. In many embodiments, individualized stimulus combinations are determined based on data generated from applying a panel of targeted single stimuli to single samples including but not limited to cancer cell lines and individual patient samples. In some embodiments, malignant subpopulations of a tumor are identified from an input data set to define intratumoral heterogeneity and thereby disentangle complex signaling changes in heterogeneous tumors in the presence versus absence of stimuli. Once the subpopulations are identified, stimulus effect in terms of the probability that a stimulus $S_j$ has altered intracellular marker $M_i$ in subpopulation k can be computed. In several embodiments, the computations are performed using linear models. In various embodiments, the computations are performed using Bayesian analysis. Given these probabilities, a nested-effects model, or nested-effects network, integrating the effects for each marker across all the subpopulations across all stimuli can be created. The nested-effects model can be represented as a graphical network where the nodes are the stimuli and edges relate to shared effects. All stimulus combinations can then be scored and ranked based on the nested-effects model. In a variety of embodiments, the stimulus combinations are ranked to select the minimum number of stimuli that produces the maximal desired effect, under the assumption that less stimuli lowers treatment related toxicities and costs. Based upon these scores, a physician can commence a regimen of treatment involving stimulus combinations that are specifically targeted to the treatment of an individual patient's tumor. As can readily be appreciated by a person having ordinary skill in the art, stimuli can refer to any of a number of compounds that can produce a response in cells, such as but not limited to drugs, bio-molecules, or any other stimuli as appropriate to the requirements of a given application. While specific discussions will be directed to using drugs as stimuli, the systems and methods described below can be used with any number of stimuli in accordance with a given application.

In many embodiments, single-cell drug screening perturbation data and nested effects models are used to identify optimal drug combinations for a single tumor while also taking into account the tumor's intratumoral heterogeneity. The identification of optimal drug combination strategies can account for two types of intratumoral heterogeneity: (1) variation in the distributions of biomarker responses within a single tumor sample in a form of a mean and variance, and (2) heterogeneity from distinct tumor subpopulations that respond differently to drug perturbations. In some embodiments, the identified drug combinations are optimized to contain the minimum number of drugs that produces the maximal desired effect, under the assumption that less drugs lowers treatment related toxicities and costs. In other embodiments, the identified drug combinations are optimized to produce the maximal desired effect while avoiding adverse side effects from more generally formulated drug combinations.

A conceptual view of drug combination optimization principles is shown in FIG. 1. A potential combination therapy response at the single-cell level can result in a variety of possible desired effects in a single cell. For example, administration of the drug combination green+red 102 might result in intracellular effects that are (i) disjoint 104, (ii) superset 106, 108, (iii) intersection 110, or (iv) dominant 112, 114. From these results, it could be inferred that, to eradicate the single cell, either a single drug would be needed (in the case of intracellular effects 106, 108, 112, and 114) or both drugs (in the case of intracellular effects 104 and 110). Because a tumor is a collection of cell types, aggregating across the cell types would be necessary to identify the optimal drug combination for the tumor of an individual patient. For example, targeting the entire population 116 of cancer cells with red, green and blue targets using only drugs green+red 118 will miss cells with unique blue targets 120, making it necessary to use all three drugs 122. However, if the blue effects are shared with the green and red effects, then all three drugs 124 are suboptimal compared to using only two drugs 126.

In many embodiments, single cell perturbation responses to a panel of monotherapies are used as input data and a drug-nested-effects model and the scored-sorted list of drug combinations are returned as an output. In other embodiments, drug combination data are also used and synergistic drug combination effects can be accounted for within the nested-effects model framework. The collected perturbation drug response in the form of data associated with intracellular signaling markers, before and after monotherapy, can be assumed to serve as a surrogate for drug effectiveness. In several embodiments, data representing drug-induced perturbation responses of a single tumor across numerous monotherapies are collected using mass spectrometry (also known as cytometry by time-of-flight or "CyTOF"), a technology that combines the cellular analysis principles of traditional fluorescence-based flow cytometry with the selectivity and quantitative power of inductively coupled plasma-mass spectrometry. CyTOF is a multiparametric single-cell technology that can measure intracellular and surface markers at the level of single cells for hundreds of thousands of cells in a sample before and shortly after treatment. In mass spectrometry systems, single cells can be labeled with antibodies that are tagged to stable isotopes of rare earth metals. The metal-chelated antibodies can require minimal signal compensation between the different metal tags, allowing numerous independent measurements on single cells. During data acquisition, detection of the metal tags can serve as a proxy for the presence of various biomarkers of interest, such as but not limited to biomarkers associated with a drug-induced perturbation response. As can readily be appreciated by a person having ordinary skill in the art, the methods of data acquisition can vary in steps and order. As such, any method of data acquisition can be used as appropriate to the requirements of a given application.

Figure 2:
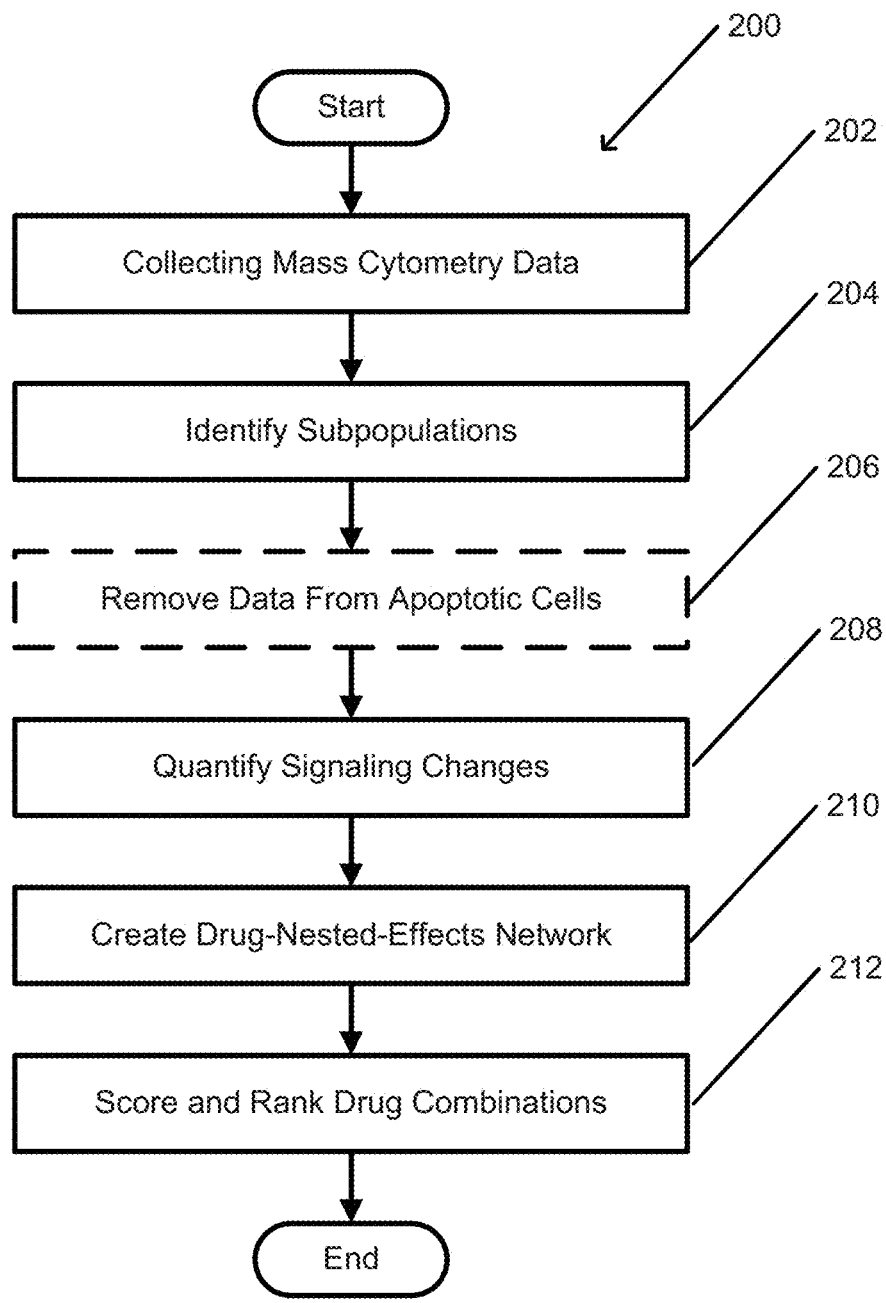
FIG. 2 conceptually illustrates a process for selecting an optimal stimulus combination in accordance with an embodiment of the invention.

One process for selecting an effective drug combination in accordance with an embodiment of the invention is illustrated in FIG. 2. The method 200 in the illustrated embodiment includes collecting (202) mass spectrometry data on a sample set of cells from a single tumor, before and after drug treatment. The data can be stored in a flow cytometry standard ("FCS") file as a data frame with rows representing the cells or events and the columns corresponding to the surface and intercellular markers of interest. In many embodiments, single-cell data is collected for a set of markers. The set of markers can include different types of markers such as but not limited to lineage markers, intracellular signaling markers, and death markers. Subpopulations can be identified (204) within the single tumor in order to account for intratumoral heterogeneity. In a number of embodiments, the subpopulations are identified using at least one lineage marker. In cases where the set of markers include a death marker, data from cells that are fully committed to apoptosis can optionally be removed (206) from the data set. Such cells can be identified and gated using at least one death marker. Changes in the intracellular signaling markers can be used to quantify (208) the perturbation effects before and after treatment within each distinct subpopulation. In a number of embodiments, intracellular signaling markers are used to identify perturbation effects before and after drug treatment within each distinct subpopulation. In many embodiments, the signaling markers are quantified in terms of the probability that a marker is differentially expressed with respect to its baseline (no drug treatment) expression. Given these probabilities of an effect for each marker in each subpopulation, the next step is to create (210) a drug-nested-effects model, which integrates the effect for each marker across all the subpopulations across all drugs. All drug combinations can then be scored (212) and ranked based on the drug-nested-effects model. Different ranking regimes can be used. In some embodiments, the method ranks the drug combination to identify the minimal combination of drugs that maximizes desired effects for an individual tumor and/or achieve effects above a predetermined threshold. In certain embodiments, the selection process can also consider known side effects of individual drugs and/or drug combinations, weighted as undesired effects. For small model networks (such as n<=5 nodes), optimizing the network for scoring drug combinations can be done exhaustively. For larger networks, the network reconstruction methods can be implemented using processes including (but not limited to) greedy search heuristics.

Although FIG. 2 illustrates an exemplary method for identifying an optimal drug combination, a person having ordinary skill in the art would understand that methods for identifying optimal drug combinations are not limited by the steps outlined above and that any other methods for analyzing single cell perturbation data to identify an effective drug combination can be utilized as appropriate to the requirements of specific applications in accordance with embodiments of the invention. For example, the process described in FIG. 2 can be extended and applied to not just MCM, but any other high-dimensional single cell drug treatment response data set. Further details of subpopulation identification, nested effects modeling, and drug combination scoring and ranking are discussed below.

Subpopulations Identification

Methods in accordance with many embodiments of the invention account for the possibility that a single tumor is composed of subpopulations that respond differently to a single drug. In various embodiments, the subpopulations are identified through manual gating. In other embodiments, automated processes, including but not limited to unsupervised subpopulation identification algorithms, are used to identify subpopulations. In some embodiments, processes including (but not limited to) clustering and a decision tree are used to automatically identify relatively homogeneous subpopulations for before and after drug treatment perturbation analysis of intracellular signaling. The strategy, named CCAST for Clustering, Classification, and Sorting Tree, can be described as an automated model framework to identify a gating strategy using a data-derived decision tree representation to isolate subpopulations from single cell data with greater homogeneity compared to manual gating. The decision tree can also be used to match corresponding homogeneous partitions across the treatment samples by pooling all samples into one data matrix and applying CCAST on the pooled data. The purity of the subpopulations can depend on the lineage markers selected for clustering.

For each population, CCAST can also gate out the cells in which apoptosis has been initiated, leaving surviving cells whose signaling is taken to be informative of a pre-apoptotic response. In many embodiments, a pre-specified death marker is used to gate out the apoptotic cells. In other embodiments, the most statistically significant death marker is used.

Figure 3A:
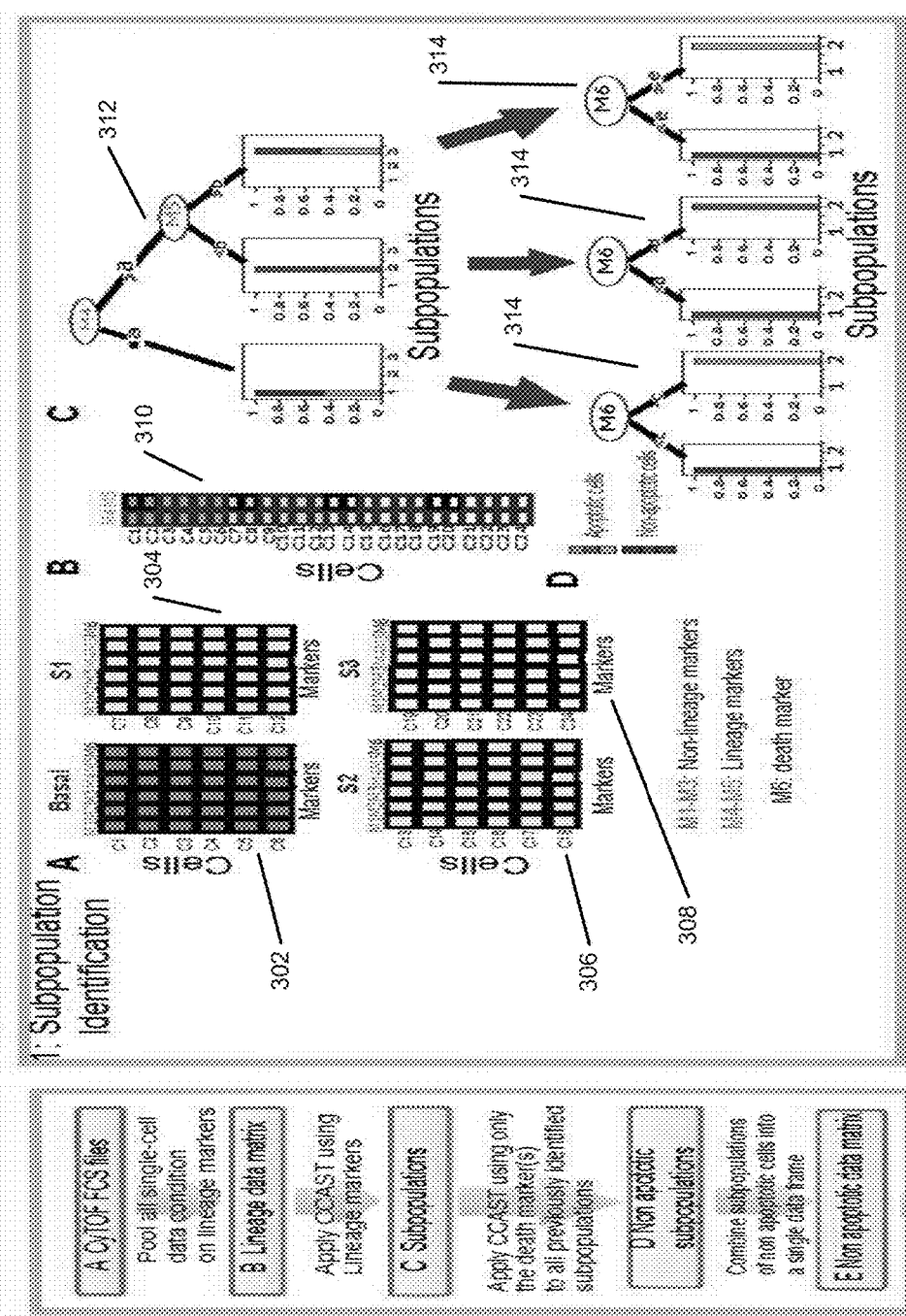
FIGS. 3A-3C conceptually illustrate the use of CCAST and nested-effects models to score and rank stimulus combinations in accordance with an embodiment of the invention.

FIG. 3A illustrates the use of CCAST in identifying subpopulations on a hypothetical mass spectrometry data set. In the exemplary embodiment, an individual sample is analyzed under no treatment (basal state) and following treatment by each of three hypothetical drugs $S_1$, $S_2$, and $S_3$. Under each condition, single-cell data are collected for six hypothetical markers $M_1$-$M_6$ measured per cell. The input data set is the format of FCS files produced by CyTOF where rows represents cells or events and the columns correspond to markers of interest. Each FCS file or data matrix would correspond to a single perturbation. Four different data frames show measurements of the markers of the cells in four different states, which includes the baseline 302 (before drug treatment), after treatment of drug $S_1$ 304, after treatment of drug $S_2$ 306, and after treatment of drug $S_3$ 308. CCAST then pools all the single-cell data across all the conditions (basal and drug treated) into a single data frame 310 (only lineage markers shown). Next, lineage markers $M_4$ and $M_5$ are used to identify subpopulations. In the illustrated embodiment, a decision tree 312 is used to identify three subpopulations, color-coded as green, red, and blue. In many cases, it is desirable to identify non-apoptotic against apoptotic cells within each subpopulation because the changes in the intracellular signaling differ in apoptotic versus non-apoptotic cells. In the illustrated embodiment, death marker $M_6$ is used to gate out the apoptotic cells. This gating process 314 can be depicted as further branches of the decision tree. After the identification and gating step, the signaling expression measurements for each marker in each non-apoptotic subgroup are summarized into a data frame 316 (shown in FIG. 3B), with rows corresponding to the intracellular markers ($M_i$) and the columns to the treatments (including basal). The signaling expression measurements for each marker $M_i$ from drug $S_j$ condition on subpopulation k can be denoted as $M_{ijk}$. Cells for each marker in each subpopulation can form a replicate data under each drug treatment, allowing for averaging of the signaling marker expressions from each subpopulation and statistical testing of differential treatment effects for each marker using linear models.

Although FIG. 3A illustrates an exemplary method for identifying subpopulations within a single tumor, a person having ordinary skill in the art would understand that methods for identifying subpopulations are not limited by the steps outlined above and that any other methods can be utilized as appropriate to the requirements of specific applications in accordance with embodiments of the invention.

Drug-Effects Model Reconstruction using Nested Effects Modeling

Once the subpopulations are identified, the drug effect can be computed in terms of the probability that a drug $S_j$ has altered intracellular marker $M_i$ in subpopulation k. The probability of an effect on marker $M_i$ by drug $S_j$ conditioned on subpopulation k can be represented by $E_{ijk}$. With respect to the mass spectrometry data in subpopulation k, the probabilities can be estimated using linear models. Given these probabilities of an effect for each marker in each subpopulation, a drug-nested-effects model that integrates the effects for each marker across all the subpopulations across all drugs can be created.

One such tool for estimating these probabilities (log-odds) is the "limma" package in Bioconductor, an open source software for bioinformatics. For each subpopulation, estimates can be derived from a moderated t-statistic for a particular marker $M_i$ with the variance component estimated across all the markers. The B-statistic (lods or B) output from limma, which is the log-odds that the marker is differentially expressed, can be used to derive the probability of $E_{ijk}$ of a marker $M_i$ being differentially expressed under drug $S_j$ condition on subpopulation k. Assuming $B_{ijk}$ and $E_{ijk}$ correspond to the log-odds and probability estimates, respectively, for marker $M_i$ to be differentially expressed after drug treatment $S_j$ in subpopulation k, $$\log\left(\frac{E_{ijk}}{1-E_{ijk}}\right) = B_{ijk}. \quad (1)$$

This implies $$E_{ijk} = \frac{\exp(B_{ijk})}{1+\exp(B_{ijk})}. \quad (2)$$

In many embodiments, nested-effects modeling is used to generate a graphical model of drugs representing the relationships between drugs and markers across subpopulations. Nested-effects models can be used for the analysis of non-transcriptional signaling network as well as transcriptional regulatory networks. In one framework, perturbed genes in the signaling pathway are called S-genes while the genes that show expression changes in response to perturbation are called E-genes. In this framework, if the downstream effects resulting from silencing gene B are a noisy subset of those resulting from silencing gene A, nested-effects models infer that gene A operates upstream of gene B in a pathway. In summary, a nested-effects model can be a directed and possibly cyclic graph that connects the S-genes with edges representing subset relationships. As can readily be appreciated by a person having ordinary skill in the art, the nested-effects model methodology can be implemented in a variety of ways including but not limited to bioinformatics software such as Bioconductor.

Figure 4:
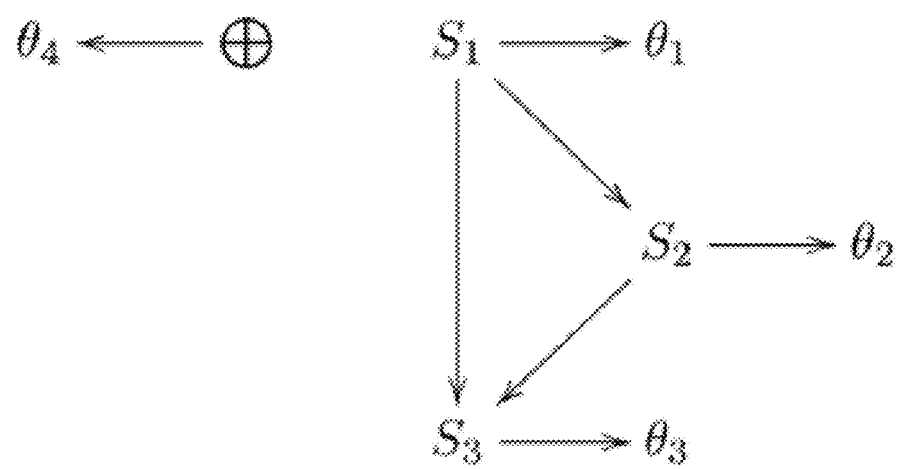
FIG. 4 conceptually illustrates a complete model parameterization for three stimuli in accordance with an embodiment of the invention.

Applying the nested-effects model framework described above to methods in accordance with many embodiments of the invention, S-genes can be defined as drug interventions and E-genes as targeted intracellular markers. If single drug interventions are denoted by $S=S_1, \ldots, S_n$, a directed edge from $S_1$ to $S_2$ can indicate that markers affected by drug $S_2$ are also affected by drug $S_1$. This can define a subset relationship on pairs of drugs and thus transitive relationships are expected for more than two drugs mathematically represented as a transitively closed graph or adjacency matrix that defines a partial order on the drugs S. Assuming that the effect data E is a 2D data matrix with number of rows of E representing m marker effect vectors, a nested-effects model includes the transitively closed graph $\phi$ and the parameters for the allocation of specific desired effects to drugs denoted as E-marker positions $\Theta$. Specifically, $\Theta=\{\theta i\}_{i=1}^{m}$ with $\theta_i \in \{1, \ldots, n\}$ and $\theta_i = j$ if $M_i$ is attached to $S_j$. FIG. 4 illustrates a complete model parameterization for three drugs with all E-marker-effect positions. Nested-effects models can be extended by including an additional node denoted by ED, which is not connected to any of the drug intervention schemes. E-markers can be linked to this node; if their effect pattern does not match any of the $\theta_1$ in $\phi$. Markers linked to the ⊕-node are usually excluded from the model.

Given the estimated effect data matrix E, the likelihood of the model can be calculated and maximized. A given network $\phi$ is usually scored by estimating the posterior probability given the data E, $P(\Phi|E)$. According to Bayes rule, the posterior probability can be written as $$P(\Phi | E) = \frac{P(E | \Phi)P(\Phi)}{P(E)}, \quad (3)$$

where P(E) is a normalization constant that does not depend on $\Phi$. Consequently, the marginal likelihood $P(E|\Phi)$ together with the network prior $P(\Phi)$ play the central role in the inference. An exhaustive search on all model network structures can depend on scoring each network by the marginal likelihood.

Given effect data E, the marginal likelihood can involve marginalization over the whole parameter space $\theta$.

$$P(E|\Phi) = \int_{\Theta} P(E|\Phi, \Theta)P(\Theta|\Phi)d\Theta \quad (4)$$
$$= \frac{1}{n^m} \prod_{i=1}^{m} \sum_{j=1}^{n} P(E_i | \Phi, \theta_i = j).$$

The marginal likelihood $P(E|\phi, \theta)$ can be based on the assumption of conditional independence of effects given the network $\phi$ and the fact that each effect marker vector is linked to exactly one node in the network. The maximum a posteriori (MAP) estimate for $P(\phi, \theta|E)$ can be given by, $$(\hat{\Phi}, \hat{\Theta}) = \underset{\Phi, \Theta}{\mathrm{argmax}}(P(\Phi, \Theta | E)). \quad (5)$$

In an exhaustive setting, once graph $\phi$ is maximized, the E-marker positions $\theta$ can be maximized. Given a network model $\phi$, the posterior probability for an edge between drug $S_j$ and an E-marker $M_i$ is derived using equation (3). Alternatively, $\theta$ and $\phi$ can be maximized together or their optimal parameters can be estimated by a Bayesian maximum a posteriori approach. In most cases $\theta$ is treated as nuisance parameters that are integrated out to make predictions on the perturbation space.

Figure 3B:
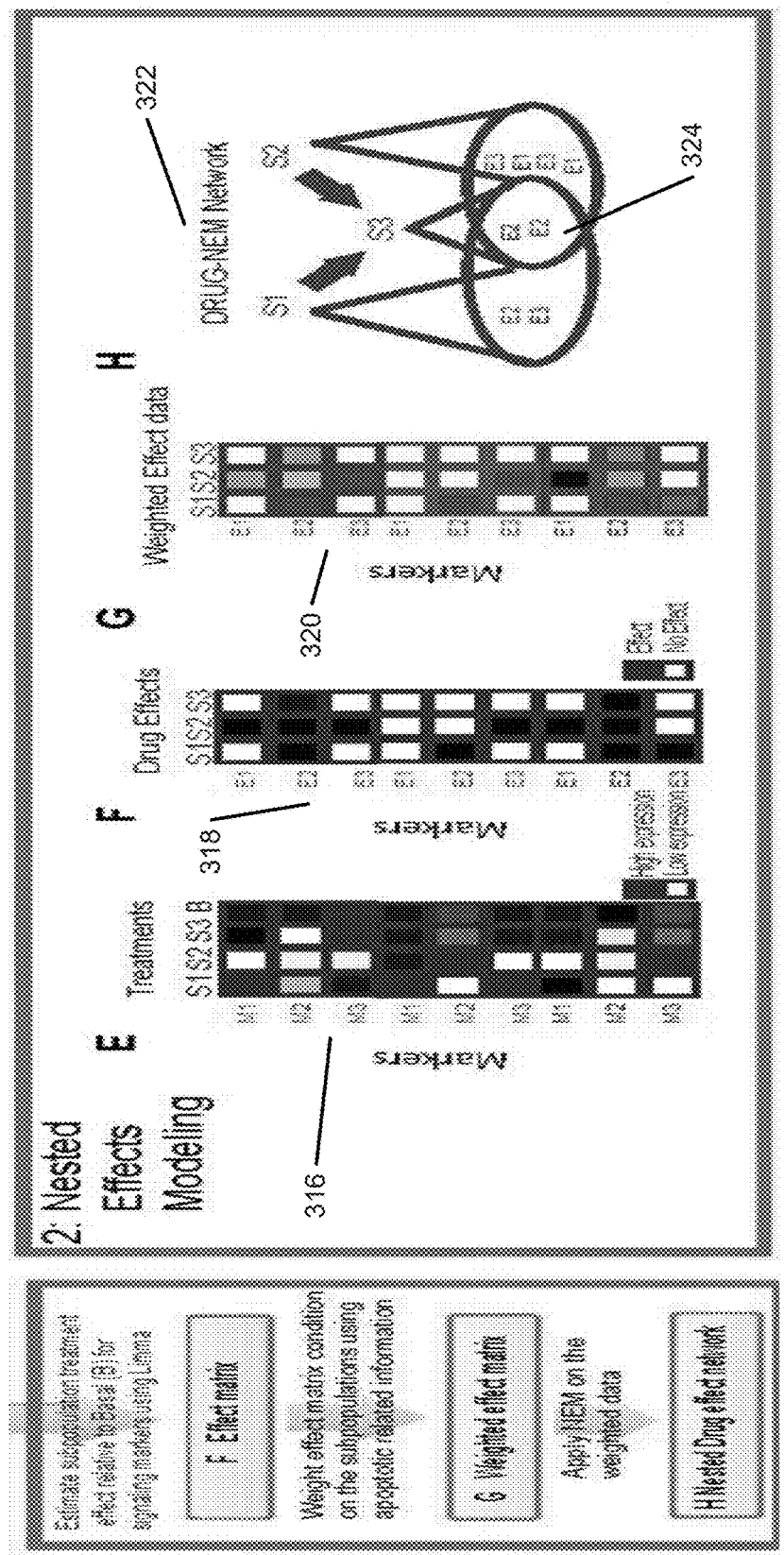

Further to the example in FIG. 3A, FIG. 3B illustrates drug-effects model reconstruction using nested effects modeling on data frame 316. The probability that a marker is differentially expressed with respect to its baseline (no treatment) expression can be estimated under each drug using Bayesian linear models. For each subpopulation, a probability of effects matrix can be created, where white versus black color-coding represents no effect versus effect, respectively, as illustrated in data frame 318. In some embodiments, the effect-probabilities can be weighted using prior knowledge related to desired effects such as but not limited to cell death on non-apoptotic subgroups, creating a weighted effects data frame 320. The probability of effects matrix for each subpopulation can be used to build a drug-nested-effects model 322 across all subpopulations. Drug-nested-effects model 322 shows the drug effect profiles from the weighted effects data frame 320 integrated across all three subpopulations. The model not only captures the subsetting relationship of the drugs, but also the assignment of the effects to each drug. In many embodiments, the drug-nested-effects model is in a form of representation where the nodes are the drugs and a directed edge between two drugs captures a subsetting of effects associated with each drug. For example, the mapping of drug-nested-effects model 322 can be represented as a directed graph between $S_1$, $S_2$, and $S_3$ with $S_3$ downstream of both $S_1$ and $S_2$. These relationships can be represented with a directed edge from $S_1$ to $S_3$ and $S_2$ to $S_3$, respectively. In summary, drugs $S_1$ and $S_2$ effects are a superset of $S_3$ effects as the $S_3$ effects 324 are inclusive under $S_1$ and $S_2$ Although FIG. 3B illustrates an exemplary method for creating a drug-nested-effects model, a person having ordinary skill in the art would understand that methods for creating drug-nested-effects models are not limited by the steps outlined above and that any other methods can be utilized as appropriate to the requirements of specific applications in accordance with embodiments of the invention.

Drug Combination Scoring and Rank

In many embodiments, the objective is to identify the minimum number of drugs that will produce the most desired intracellular effects across all subpopulations within a single tumor. One method is based on the assumption of independence in effects given estimated probability effect matrix, E. Although this method is expected to be much faster since it circumvents the need for any model reconstruction step, this approach may not be optimal when the underlying drug effect model is nested as is often expected. An alternative approach takes into account the hierarchical nature of drug-target effects using the maximized network ($\hat{\Phi}, \hat{\Theta}$) and on average can produce minimal errors between expected and predicted drug combination rankings. Both methods are discussed in further detail below.

The first method, termed the Independence Score method, treats drug effects as independent probabilistic outcomes. Given the probability that each intracellular signaling marker $M_i$ is differentially expressed under each drug intervention $S_j$ represented as data $E_{ij}$, the expected combination effect under additivity for each drug combination denoted as $Z_{ic}$ is given by $$Z_{ic} = E_{i1} + E_{i2} + \ldots + E_{ir} + \ldots + E_{i|c|} - E_{i1}E_{i2} - E_{i1}E_{i|c|} - E_{i2}E_{i|c|} - \ldots - E_{i1}E_{i2} \ldots E_{i|c|} \quad (6)$$

where $c \in \wp(S = \{1, =\wp(\})/\emptyset$ corresponds to an element of the power set of all combinations generated from the index set $\{1, \text{orr}\}$ for drugs $S_1, \ldots, S_n$ with r corresponding to the $r^{th}$ element in c and $|c|$ the cardinality of c. We then sum over a finite marker set of $Z_{ic}$ values to generate a new score denoted as $$F(c) = \Sigma_i Z_{ic} \quad (7)$$

For a drug pair for example $\{S_1 S_2\}$, $Z_{i\{1,2\}}$ is given by $E_{i1} + E_{i2} - E_{i1}E_{i2}$ and $F(\{1,2\}) = \Sigma_i E_{i1} + E_{i2} - E_{i1}E_{i2}$. When observed combination effect can be compared to expected additive effects, a standard measure of combination effectiveness known as the Combination Index (CI) can be computed, indicating synergistic (CI<1), antagonistic (CI>1) or additive (CI=1) performance. Combination Index CI for the drug pair $\{S_1 S_2\}$ is $$\sum_i \frac{E_{i1} + E_{i2} - E_{i1}E_{i2}}{E_{i12}}.$$

For a given set of drugs $S_1, \ldots, S_n$, indexed as $\{1, \text{inde}\}$, the total number of drug combinations corresponds to the cardinality of $\wp(s)/\emptyset$ given by $|\wp(S)/\emptyset| = 2^n - 1$. Letting $X_1, X_2, \ldots, X_{|\wp(S)|}$ represent the scores for each drug combination estimated by F(c), a non-decreasing ranking of the scoring distribution for these drug combinations is given by $X_{(1)} \leq X_{(2)} \leq \ldots \leq X_{(|\wp(S)|)}$ where $X_{(r)}$ is the $r^{th}$ smallest value in the distribution for $r=1, 2, \ldots |\wp(S)|$. The optimal drug combination for the Independence Score method is given by $\arg(X_{(|\wp(S)|)})$ corresponding to the combination with the maximum order score.

The second method, termed the Drugnemscore method, uses the maximum of the posterior weights $E^*_{ic} = \max(P(\theta_i = j | \hat{\Phi}, E, j \in c))$ as an estimate of desired effects from a given drug-nested-effects model $\hat{\Phi}$ associated with each intracellular signaling marker $M_i$ under each drug combination indexed by c then sums over all posterior probabilities associated with union of markers in the combination to determine F(c). For a given the nested-effects network $\hat{\Phi}$, by denoting the set of markers associated with drug $S_j$ as $A_j$, then union set of markers for a given drug combination indexed by c with r corresponding to the $r^{th}$ element in c is determined using sequences of index families of sets. Given a combination indexed by $c=\{1,2\}$, where $\hat{\Phi}_c$ forms a subgraph of $\hat{\Phi}$ with $\hat{\Phi}_2 \subseteq \hat{\Phi}_1$ and $\{A_2\} \subseteq \{A_1\}$, the smallest set containing each element of $A_r$ corresponds to the supremum of a sequence of index sets given by $\sup\{A_c\}_c = A_1 \cup A_2$. $F(\{1,2\}) =$ $$\sum_{i \in \sup\{A_{\{1,2\}}\}_{\{1,2\}}} E^*_{i1} + E^*_{i2}$$

corresponds to the sum of union of all desired effects associated with all markers attached to $\hat{\Phi}_{\{1,2\}}$.

When ranking combinations under the nested-effects model, $X_{(1)} \leq X_{(2)} \leq \ldots \leq X_{(|\wp(S)|)}$ under certain graph structures can produce ties or a step-wise distribution even under noisy data. The nested structure breaks the tie distribution forcing $\arg(X_{(|\wp(S)|)})$ in this case to $S_1$. All drug combinations having a score of $X_{(|\wp(S)|)}$ are identified. This corresponds to a new index family of elements of $\wp(S)$ denoted here as $R_{X_{(|\wp(S)|)}}$ where $R_{X_{(|\wp(S)|)}} = \{c | c \in \wp(S), X_{(|\wp(S)|)} = F(c), \forall c\}$. The optimal combination from a tie is then given by $\{c \| c \| = \min\{|d|, \forall d \in R_{X_{(|\wp(S)|)}}\}\}$.

Methods in accordance with many embodiments of the invention can use prior information to generate a weighted effect matrix to score drug combinations. It can be expected that different drugs can trigger different survival intracellular marker responses across subpopulations, which may or may not be associated with a particular desired phenotypic effect such as but not limited to cell death. This prior information can be incorporated by weighting each $E_{ijk}$ to generate a new effect data matrix representing a more desired effect. One method of weighting involves weighting either up or down regulated effects for scoring. Another method can involve weighting using up regulation of death signaling markers. Generally, a positive drug signaling effect is expected to correlate with increase in expression of death signaling markers. One-sided p-values from testing can be used if the drug will increase the expected expression of the death signaling protein in each subpopulation within the limma framework, thereby giving less weight to drug effect changes in pro-survival cells or subpopulations. The normalized inverse one-sided p-values can be used as weights. Another method of weighting involves weighting the effect probabilities $E_{ijk}$ using observed distribution of dying cells. In the event that changes in the death signaling markers are highly non-significant, an alternative strategy is to use the distribution of cells in the dying state as possible estimates to weight each $E_{ijk}$. The motivation for such an approach is that each individual drug might trigger a different proportion of cells in each subpopulation to transition to a death state, thereby introducing a heterogeneous death response distribution, which can be normalized and used as prior weights to generate the weighted effect matrix. As can readily be appreciated by a person having ordinary skill in the art, ways of weighting $E_{ijk}$ are not limited to those described above and any of a number of methods can be used as appropriate to the requirements of a given application. For example, a subpopulation with stem cell-like properties within the tumor can be targeted, and the $E_{ijk}$ are weighted accordingly. In some embodiments, subpopulations of healthy cells are weighted to avoid inducing cell death.

Figure 3C:
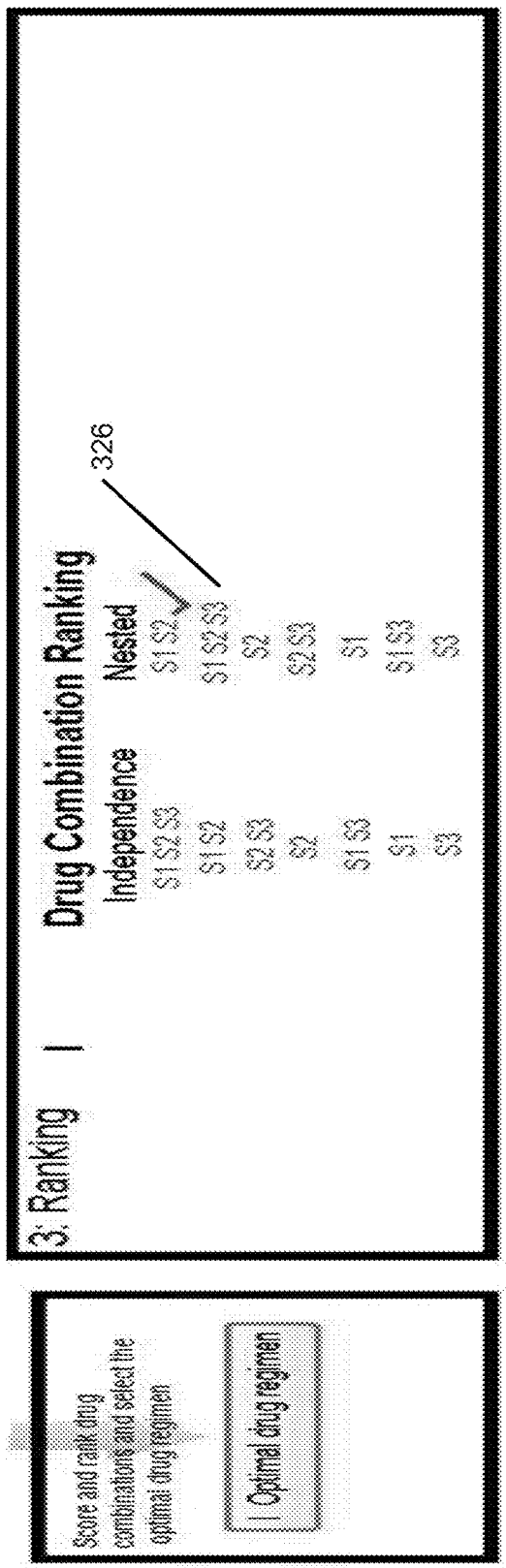

Further to the example in FIGS. 3A and 3B, FIG. 3C illustrates an exhaustive ranking 326 for all drug combinations of drugs $S_1$, $S_2$, and $S_3$ assuming equal contributions across subpopulations under both independence and nested effects assumptions. In the exemplary embodiment, the drug combinations are scored and ranked under the additive nested effects assumption using the hierarchy and posterior weights from the drug-nested-effects model 322 to determine the combination that maximizes the objective criteria. For comparison purposes, a scoring strategy based on an independence additive effects assumption, whereby each combination of drugs were scored using only the probability of effect matrix without prior knowledge of the structure of drug interactions using the drug-nested-effects model 322. Note that although the combinations $S_1+S_2$ and $S_1+S_2+S_3$ affect all markers in all subpopulations, $S_1+S_2$ does so with only two drugs and therefore scores higher using the nested effects instead of the independence effects assumption, which is less evident from the scoring using the independence assumption on noisy data.

Although FIG. 3C illustrates an exemplary method for scoring and ranking drug combinations, a person having ordinary skill in the art would understand that methods for scoring and ranking drug combinations based on a drug-effects model are not limited by the steps outlined above and that any other methods can be utilized as appropriate to the requirements of specific applications in accordance with various embodiments of the invention.

EXEMPLARY EMBODIMENTS

Figure 5A:
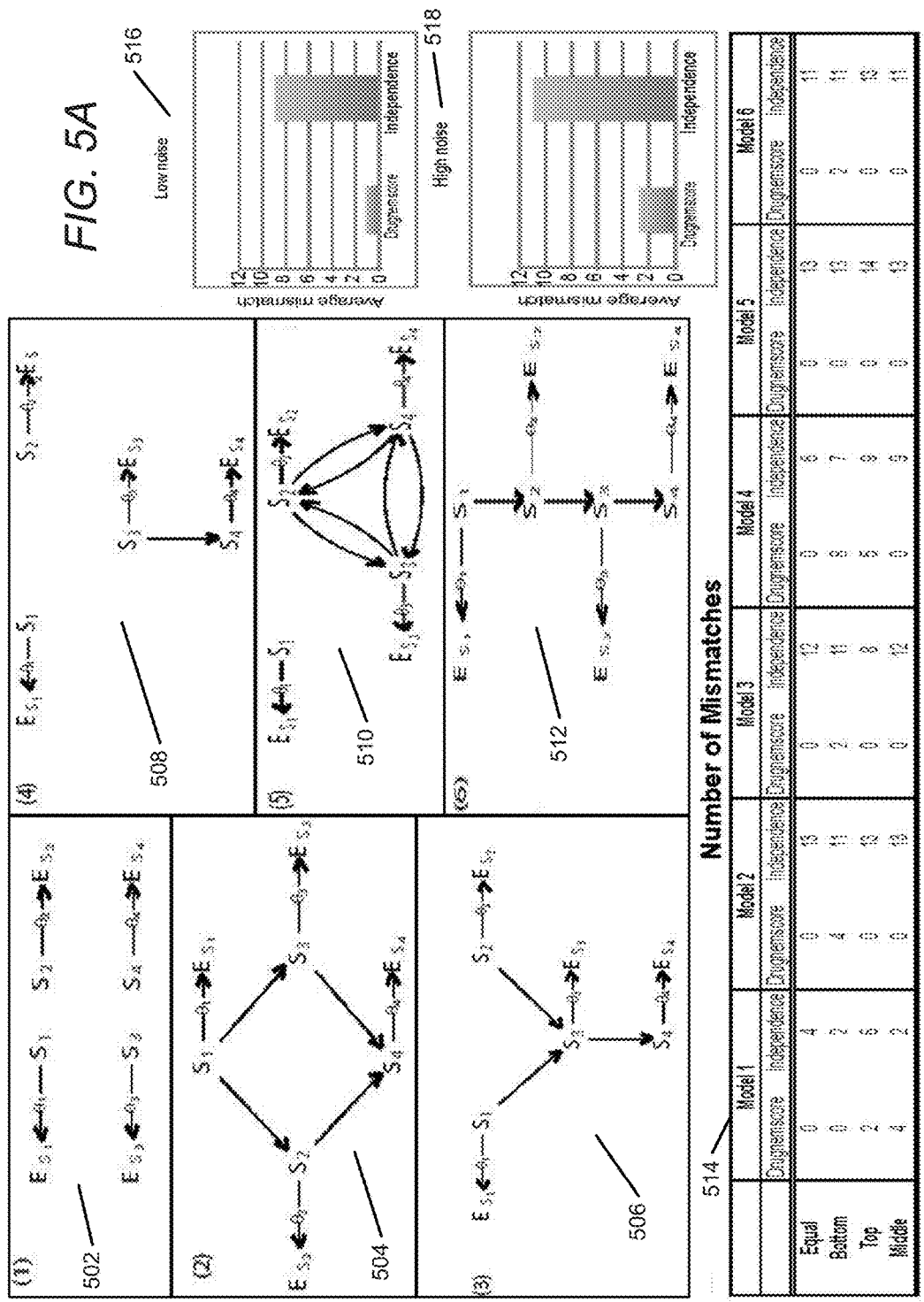
FIGS. 5A-5B conceptually illustrate a simulation analysis in accordance with an embodiment of the invention.

To show that optimizing drug combinations by integrating over the nested effects assumption can perform better on average than under additive independent assumptions using simulated homogeneous and heterogeneous mixtures of effects derived from different graphical drug model structures, a sensitivity analysis can be performed. FIG. 5A shows six different network models for simulation analysis. In network model 502, all drugs target disjoint signaling markers generating distinct effect profiles. In network model 504, all drug effects are nested within a single drug $S_1$ in addition to the effects of $S_4$ nested within the effects of $S_2$ and $S_3$. In network model 506, the effects of drugs $S_1$ and $S_2$ are a superset of the effects of drugs $S_3$ and $S_4$. Network model 508 corresponds to the model with a disconnected component ($S_1$ and $S_2$) and connected components ($S_3$ and $S_4$) with the effects of $S_4$ nested within $S_3$. Network model 510 corresponds to the model with a single disconnected drug $S_1$ and a fully connected component ($S_2$, $S_3$ and $S_4$). The expected effect profiles connected to $S_2$, $S_3$ and $S_4$ under such a model can be considered equivalent. Network model 512 corresponds to the model with a linear nested network with $S_1$ on top. For each network, expected effects are attached in four different ways: "Equal" represents approximately equally distributed effects across nodes, "Bottom" represents more effects attached to the bottom node(s), "Top" represents more effects attached to the top node(s), and "Middle" represents more effects attached to the middle node(s) when appropriate. Taken together, there can be twenty-four simulation conditions.

Methods for optimizing drug combinations such as those described above are used to analyze each simulated data based on the two scoring methods denoted as "Independence" and "Drugnemscore" for additive independence and nested models, respectively. Both scoring approaches are compared by matching each ranking distributions with respect to the true (expected) ordering of all drug combinations. The number of mismatches between the truth and predicted orderings are counted for the two scoring metrics described above for all twenty-four simulated network models. Table 514 summarizes the mismatch analysis for all six networks under various expected effect distributions and under low noise level for independence and nested models. As can be seen, table 514 shows that the nested model (Drugnemscore) outperforms the independence model (Independence) in 22 of the 24 conditions. On average the Drugnemscore metric has the smallest number of mismatches compared to the Independence metric in both low (graph 516) and high (graph 518) noise settings.

Figure 5B:
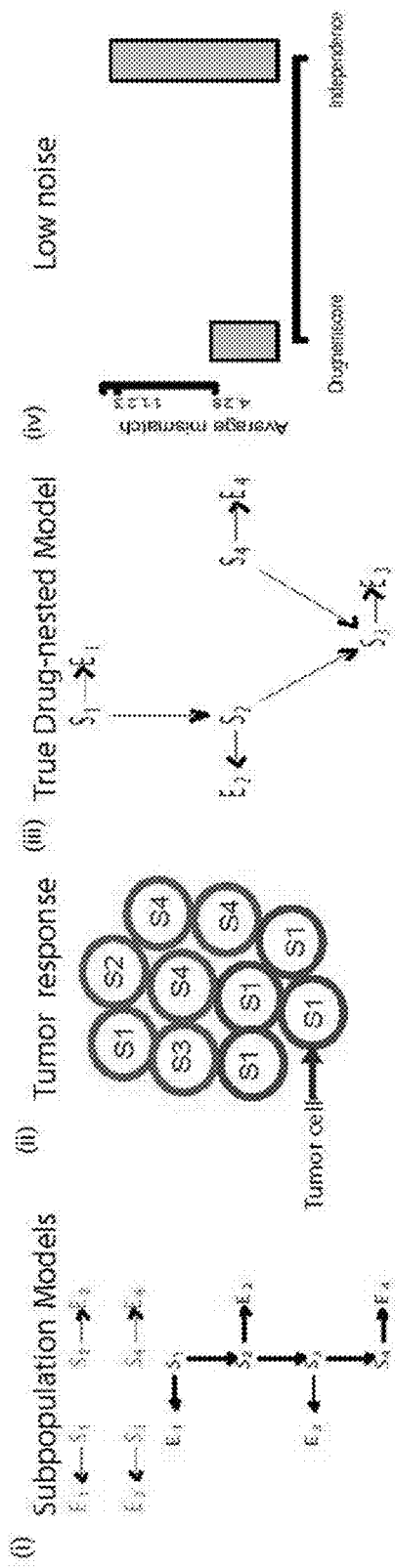

FIG. 5B illustrates the sensitivity analysis from one simulated heterogenerous condition derived by combining network model 502 with network model 512. The resulting subpopulation model 520 can be used to generate a possible heterogeneous phenotype representation 522 for the dominant drugs with effects on the entire tumor sample. As shown, the blue cells have a dominant $S_1$ effect since all the drug effects are nested within $S_1$ and each of the four drugs have effects that are dominant in at least one of the cells within the green subpopulation with $S_4$ having the strongest response. Drug combinations can be scored using simulated noisy data from the underlying true nested model 524, and estimating the average mismatch between the predicted and truth as described above, produces a bar plot 526 that shows a superior performance of the nested model (Drugnemscore) versus the independence model (Independence) based on the least number of mismatches. Optimizing the objective function under independent effects assumptions can produce a continuous monotonic function with an expected maximum, which may not be the optimal solution under certain drug network structures. In contrast, optimizing the objective function under the nest effects assumptions can produce a monotonic step-wise function, whereby with equivalent scoring strategies (ties) can be further assessed based upon other factors such as the number of drugs. In the current embodiment, the optimal nested solution is the highest scoring combination with the minimum number of drugs.

In one exemplary embodiment, a panel of single drug candidates were tested on HeLa cells and the resulting data was analyzed to find an optimal drug combination. Particularly, three small molecule inhibitors were considered as candidates to be combined with TRAIL for treating HeLa cells. TRAIL, a death ligand member of the TNF ligand superfamily is a potent stimulator of apoptosis and has been considered an attractive cancer therapy. However, poor results from TRAIL alone are likely due to complex mechanisms, possible pathway dependent resistance mechanisms to TRAIL, and possibly intratumoral heterogeneity. Ongoing interest in TRAIL is now more focused on its part within a drug combination strategy. Critical signaling markers associated with TRAIL are illustrated in FIGS. 6A and 6B.

Once TRAIL binds to its cell surface receptor, it can recruit pro-caspase8 and FAS-associated protein with death domain ("FADD") to form a death-inducing signaling complex ("DISC") that triggers a relay of signals leading to cell death (shown in FIG. 6A). The canonical view of apoptotic signaling down stream of activated Caspase 8 leads to the activation of key death effector domain of proteins such as PARP, Caspase 3, and Caspase 7. However, Bcl2 homology domain 3-interacting domain death agonist ("BID") is also a target for the active Caspase 8. Cleaved BID ("tBID") also activates the apoptotic pathway by binding to BAX, Bcl2 homologous antagonist/killer ("BAK") or prosurvival Bcl2 family proteins and serves to amplify the death receptor apoptotic signal. Moreover, TRAIL has been shown to mediate several signal transduction pathways leading to cell proliferation, cell survival instead of cell death. FIG. 6B summarizes most of the key players involved in the TRAIL signaling pathway.

Using CyTOF, single-cell data on HeLa cells were collected with no treatment and in response to four treatments. Three small molecular inhibitors were considered as candidates to be combined with TRAIL: (1) MEK inhibitor ("GSK") GSK1120212, which is a potent and highly specific MEK1/2 inhibitor, (2) pP38MAPK inhibitor ("SB"); SB203580, which directly binds competitively to the ATP site of the enzyme of p38 MAPK and has been shown to be associated with reduced cell growth and apoptosis in colon cancer cells, and (3) PI3K inhibitor ("GDC"); GDC0941, which inhibits one or more of the phosphoinositide 3-kinase (PI3K) enzymes, part of the PI3K/AKT/mTOR pathway. The expected inhibited pathways are illustrated in FIG. 6C. Perturbation data at the level of single-cells were collected in response to the three interventions plus a TRAIL pathway activator on HeLa cells. The CyTOF panel consisted of twenty-four intracellular signaling proteins (shown in FIG. 6B). No surface or lineage markers were collected, and the subpopulations were manually identified.

Figure 6D:
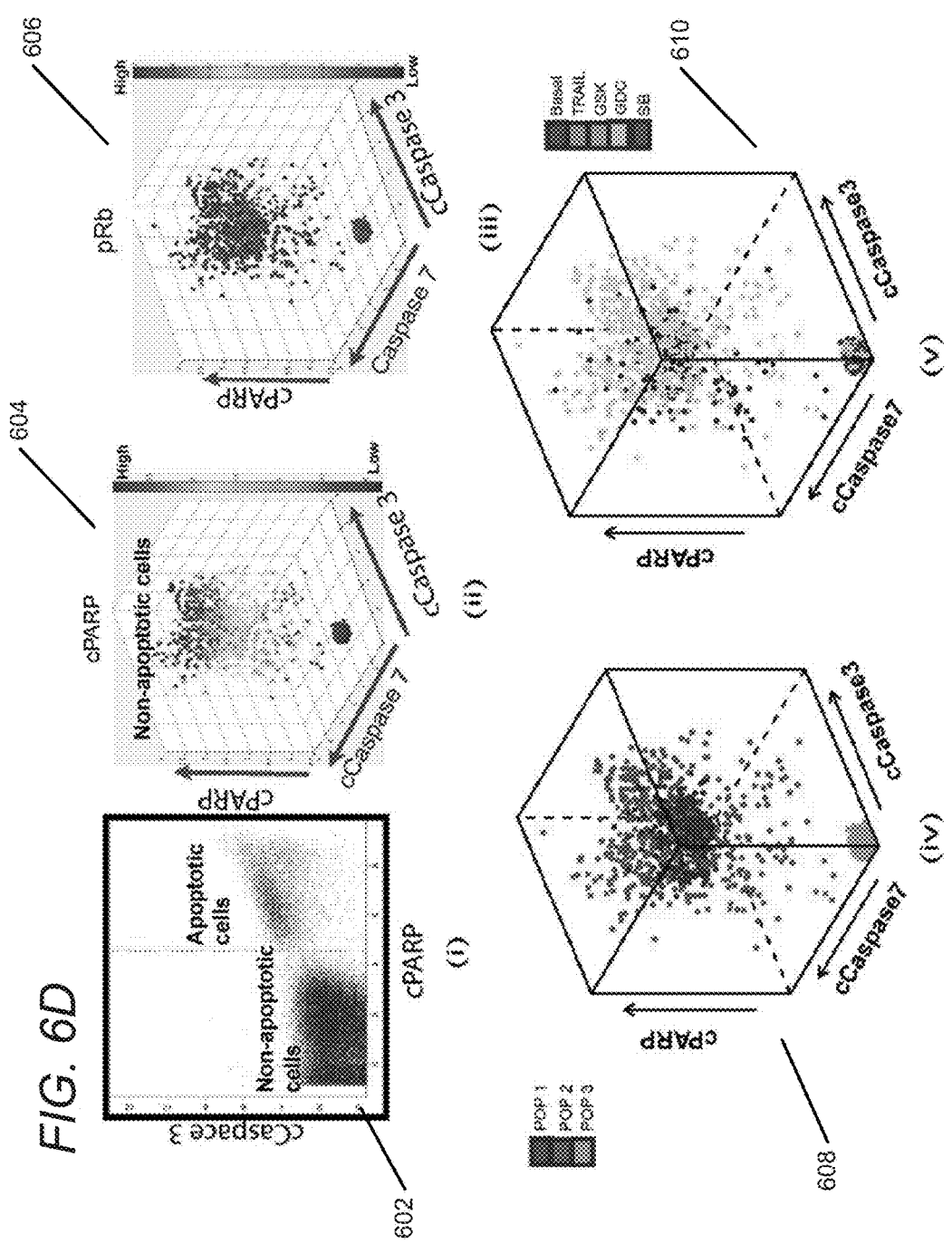

The analysis on the single-cell perturbation data of the HeLa cell line is illustrated in FIGS. 6D and 7A-7D. In the exemplary embodiment, an unsupervised analysis, CCAST, selects cPARP to identify and gate out the cells already committed to apoptosis (602). Given the lack of lineage markers in this particular embodiment, intracellular markers were manually selected to identify subpopulations. FIG. 6D, 604 shows the 3D scatterplot of two manually gated subpopulations from the non-apoptotic cells representing cPARP high and low cells. Among these cells, FIG. 6C, 606 shows that the cPARP high cells are composed of a mixture of pRb high and low cells. These three subpopulations can be regarded as "cell states" whereby HeLa cells in these different states appear to be transitioning to the death state after treatment using different mechanisms. FIG. 6C, 608 illustrates three subpopulations shown as POP1 (blue), POP2 (red) and POP3 (green). Although these cells are distributed among three states, they are actually derived independently experimentally from the five treatment conditions including basal cells (no treatment). FIG. 6D, 610 shows the distribution of the cells across all treatment conditions color-coded here as blue (Basal), light blue (TRAIL), green (GSK), orange (GDC) and red (SB). The similar distribution of cells across all three subpopulations allows us to compare signaling within and across the subpopulations.

Figures 7A, 7B:
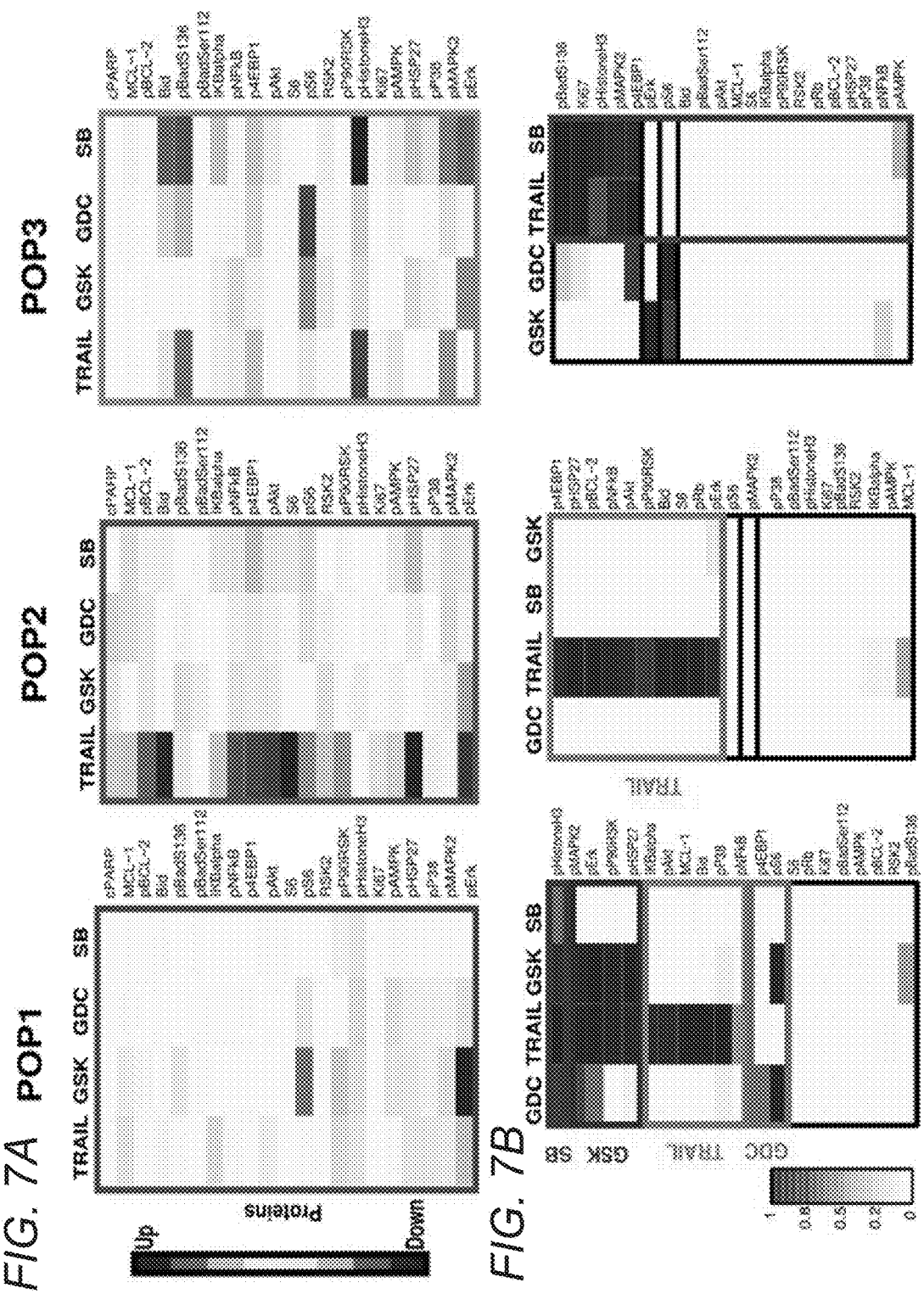
Figures 7F, 7G:
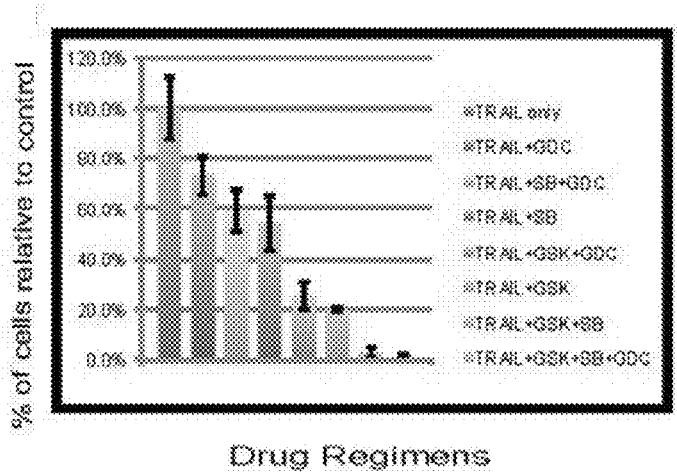

Drug combinations are scored and ranked using information received from integrating nested-drug-effects across the identified subpopulations. To quantify the uncertainty in these intracellular signaling changes, the probability that an intracellular marker is differentially expressed under a given treatment in each subpopulation can be determined using Bayesian analysis. FIG. 7A shows the heatmaps of subpopulation-normalized fold changes ("FC") of intracellular markers (which were not used to identify the subpopulations) with respect to the baseline condition across all treatments. In POP1, TRAIL and GSK each down regulate most of the survival signaling proteins, with GSK more strongly down-regulating ERK and pS6. In POP2, the strongest down regulation is by TRAIL. POP3, which corresponds to the most surviving cells, shows more up regulation than down regulation across all the treatment conditions especially under SB. The uncertainty in these intracellular signaling changes in each subpopulation are quantified using linear models to determine the probability of a protein to be differentially expressed under a given treatment. In this exemplary embodiment, to identify the optimal combination therapy only down regulated oncogenic kinase states are focused on because such a regulation state tends to correlate with increased cell death. FIG. 7B shows the heatmaps of the down regulated probability effects of all the kinases in each subpopulation. Here the rows and columns of the drug effect matrix have been sorted to show the nested relationships among drugs. This sorting can be achieved using nested-effects models. For example, in POP1, TRAIL down-regulated effects form a superset of GSK and SB effects while GSK effects form a superset of the SB effects. Within the nested-effects model framework, this directed transitively closed network in FIG. 7C infers that within POP1, TRAIL and GDC will likely have the greatest response because it downregulates the greatest number of survival markers. Although it can be inferred that three different drug-nested-effects models correspond to the three different population of cells as shown in FIG. 7C, it can be ideal to optimize drug combinations across all cells since all the cells will be treated simultaneously. Integrating the effects across all cells can result in the sorted effect data matrix shown in FIG. 7D with the drug-nested-effects model shown on the top. This integrated model looks quite different from networks derived from the individual subpopulations shown in FIG. 7C; it also differs from the predicted network that ignores intratumoral heterogeneity (FIG. 7E), where the effects are derived from averaging across all the cells. The integrated nested-effects model (shown in FIG. 7D) and associated drug combination rankings for the top regimens (shown in FIG. 7F) identifies GSK and TRAIL as a drug pair with the maximum nested desired effects.

To validate this finding that GSK and TRAIL is optimal here, an independent survival in-vitro analysis on several drug combinations involving combinations of TRAIL plus GSK, GDC, and SB using clonogenic assays can be performed. The results (shown in FIG. 7G) are presented as the percentage survival for the cells recalibrated relative to TRAIL, depicting the additional fractional killing of cells due to the addition of drugs compared to TRAIL alone. These results provide empirical evidence that any strategy that combines TRAIL with the MEK inhibitor ("GSK") is most effective on HeLa cells compared to those without. TRAIL+GSK alone killed almost 60% of the cells, and adding SB to the cocktail increased the fraction of cell kill (to almost 98%). These three regimens were consistent with the top three drug combination rankings in FIG. 7F. The top three drug combinations are tied in terms of their score. In the current embodiment, nested-effects model framework chooses the TRAIL+GSK among all the top-ranking tied combinations because this combination uses the least number of drugs.

Methods in accordance with many embodiments of the invention can identify PI3k/mTOR and ABL/Src inhibitors as a predominant optimal combination in acute lymphoblastic leukemia ("ALL"). B cell precursor ALL is a common cancer diagnosed in children and represents approximately 25% of cancer diagnoses among children younger than fifteen years. Despite dramatic improvements in clinical outcome for pediatric ALL over the last forty years, relapse remains the most significant cause of mortality in 20% of patients. Combination of targeted drugs and chemotherapy are being suggested as potential therapeutic solutions to improve these outcomes. With increasing choice of targeted therapies, there is an opportunity to identify a personalized drug combination strategy to help guide rational choice of combination therapy in pediatric ALL for the individual patient.

Figure 8C:
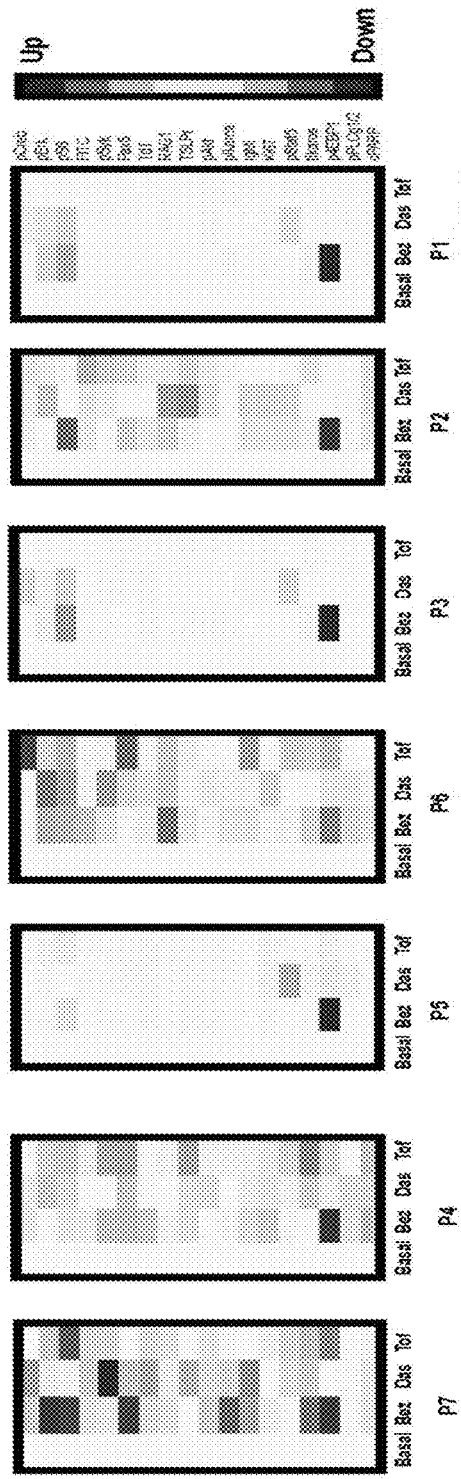
Figure 8D:
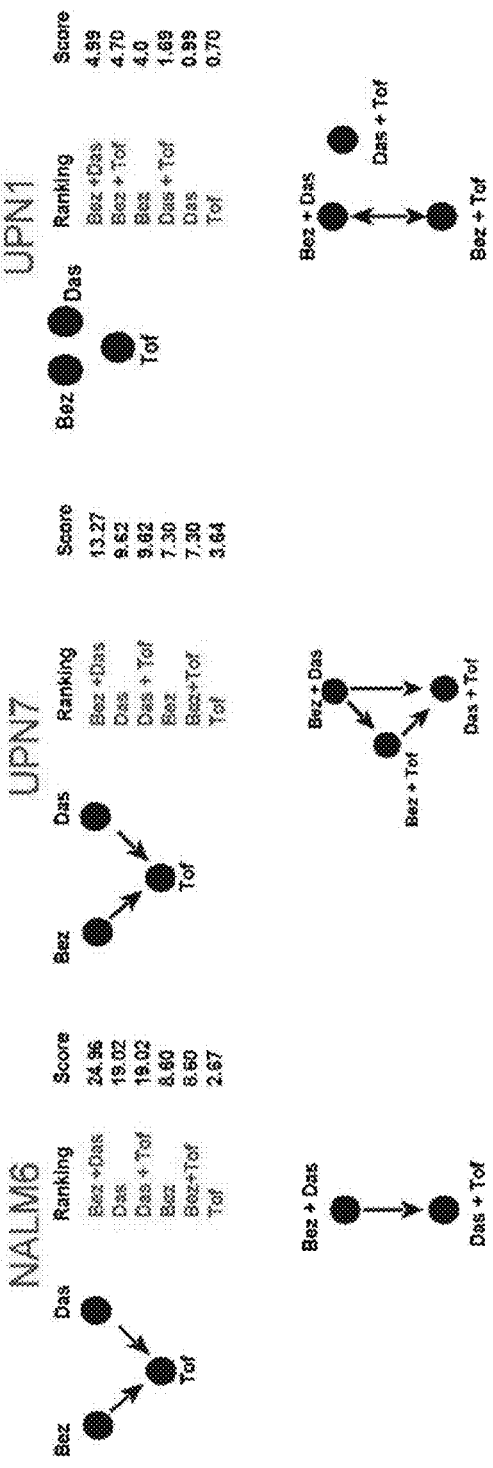
Figure 8E:
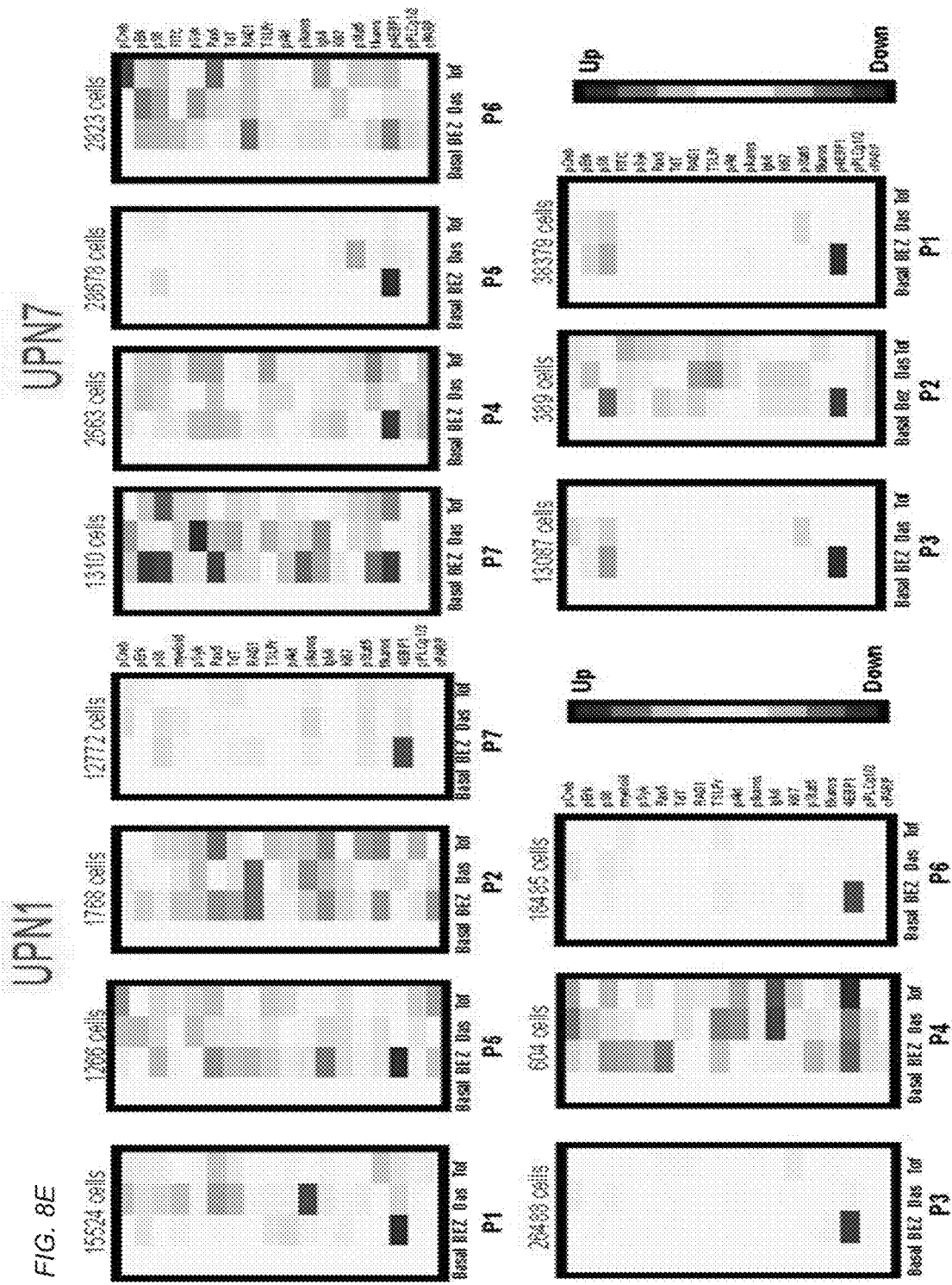
Figure 8F:
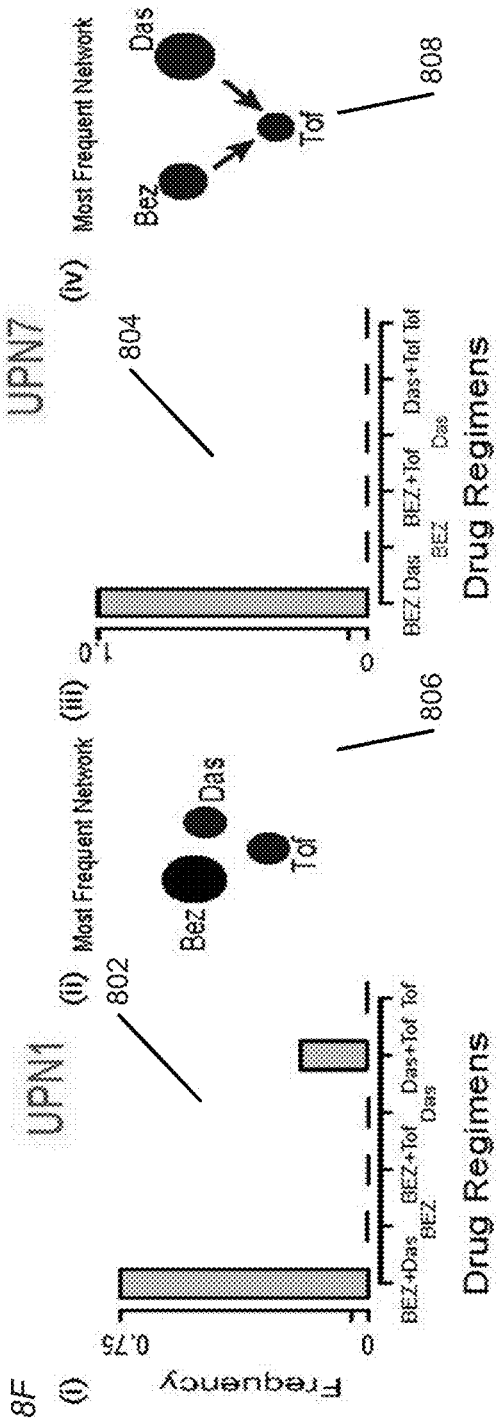

FIG. 8A-8G illustrates an in-vitro drug perturbation analysis performed at the single cell level on NALM6 cell line and two B-cell precursor Philadelphia chromosome positive Ph+ALL pediatric patients samples denoted here as UPN7 and UPN1. The NALM6 cell line is a precursor (pre)-B human cell line derived from an adult ALL relapsed patient and can be highly efficient for gene targeting by homologous recombination. Each sample was analyzed using a CyTOF panel of twenty-one B-cell lineage markers and eighteen intracellular protein expression responses. FIG. 8A summarizes all lineage and non-lineage markers in the study. CyTOF analysis were performed before and after thirty minutes of single drug treatment for three FDA approved drugs: Dasatinib (BCR-ABL inhibitor), Tofacitinib (JAK/STAT inhibitor) and BEZ-235 (PI3K/mTOR inhibitor) denoted as Das, Tof and Bez, respectively.

Figure 9:
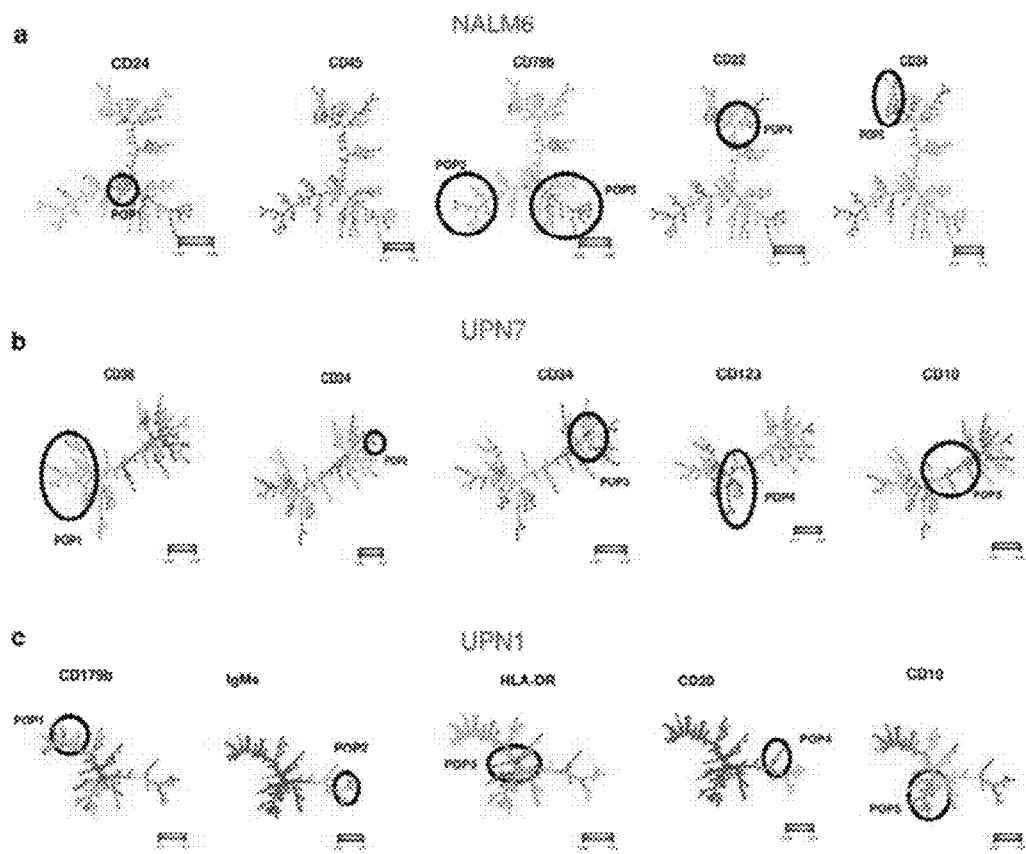
FIG. 9 illustrates SPADE analysis on the basal cells from the NALM6 cell line and two B-cell precursor Philadelphia chromosome positive Ph+ALL pediatric patient samples in accordance with an embodiment of the invention.
Figure 10A:
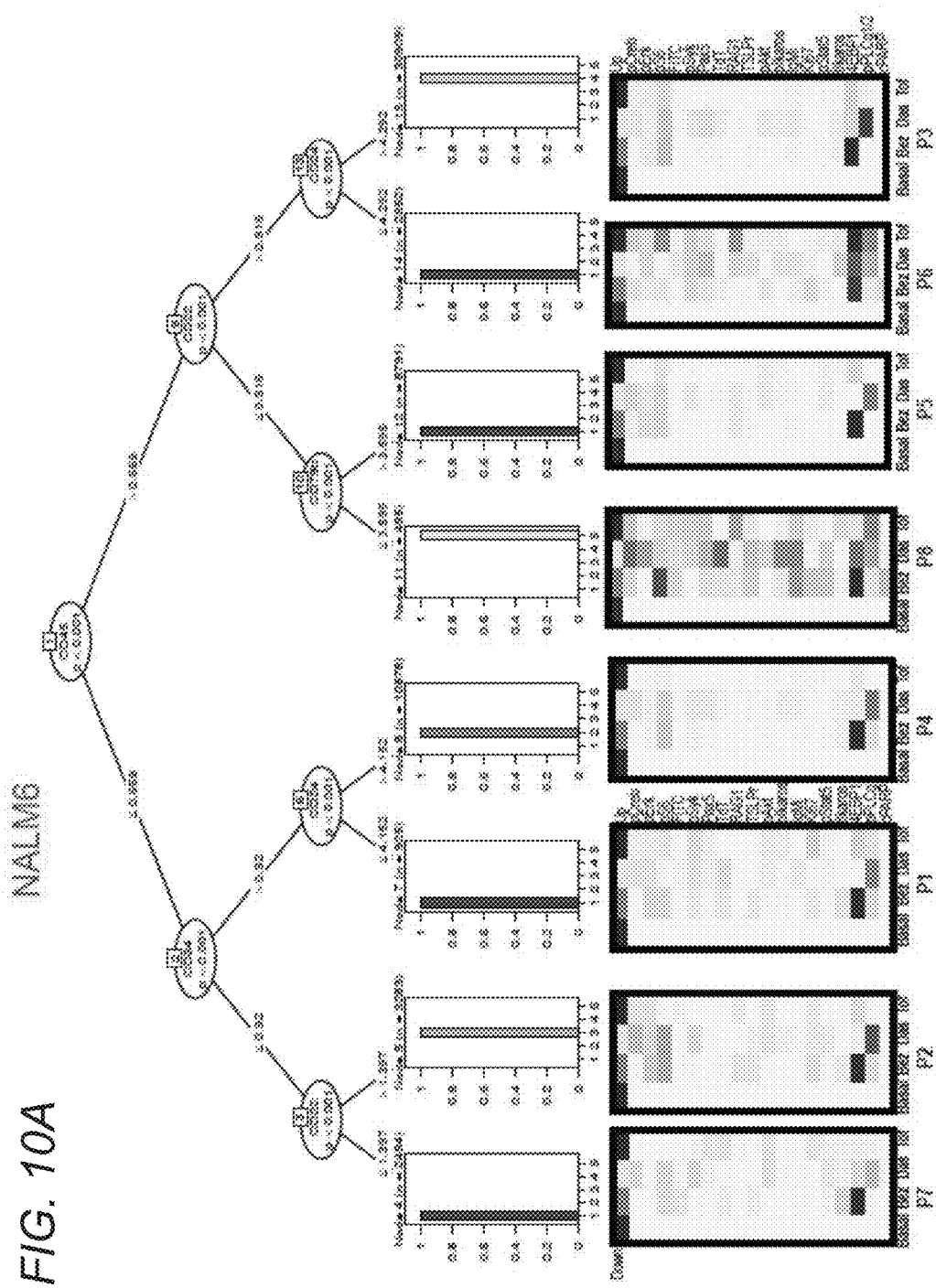
FIG. 10A-10C illustrate decision trees for the NALM6 cell line and patient samples UPN1 and UPN7 in accordance with an embodiment of the invention.
Figure 10B:
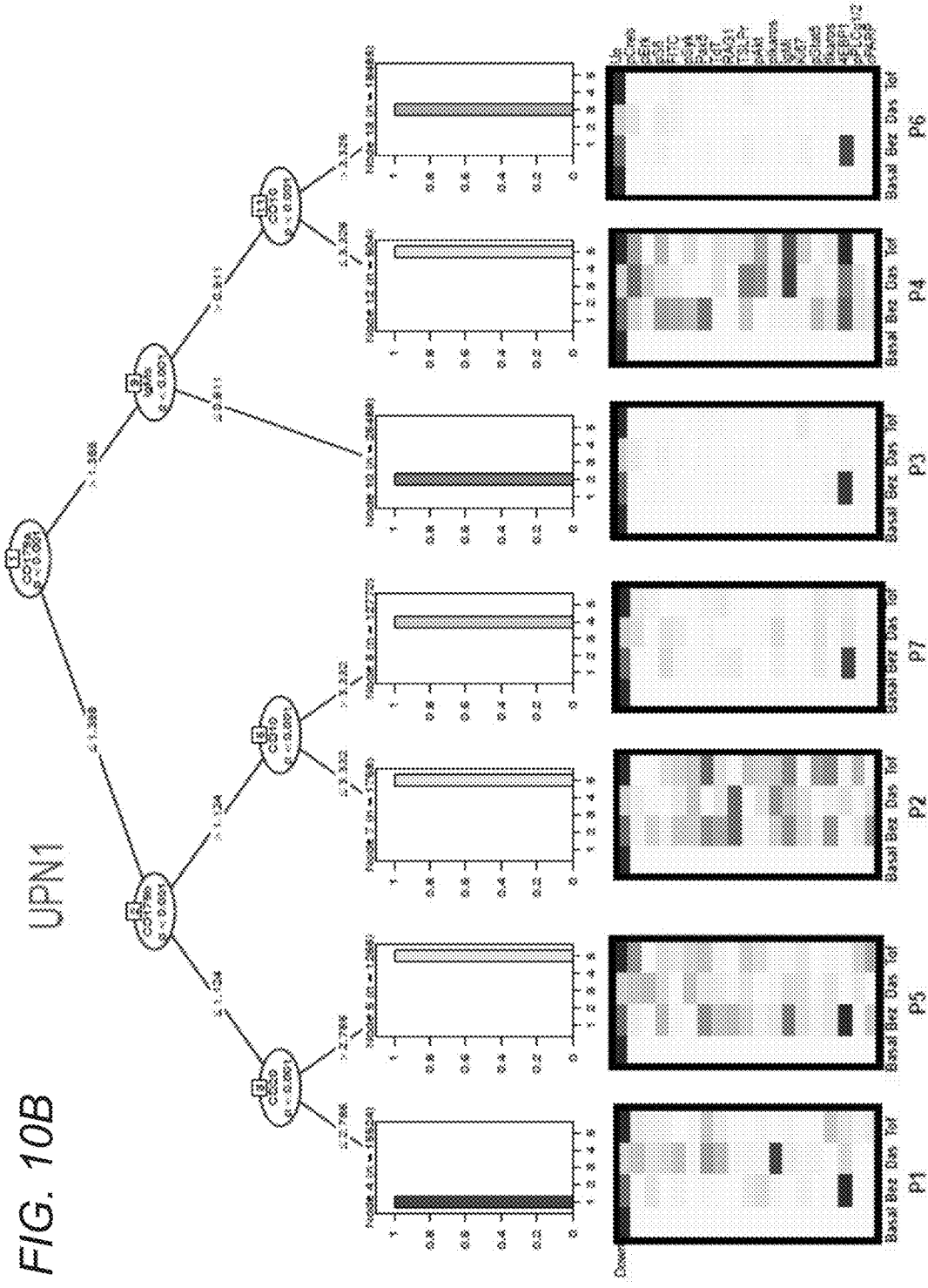
Figure 10C:
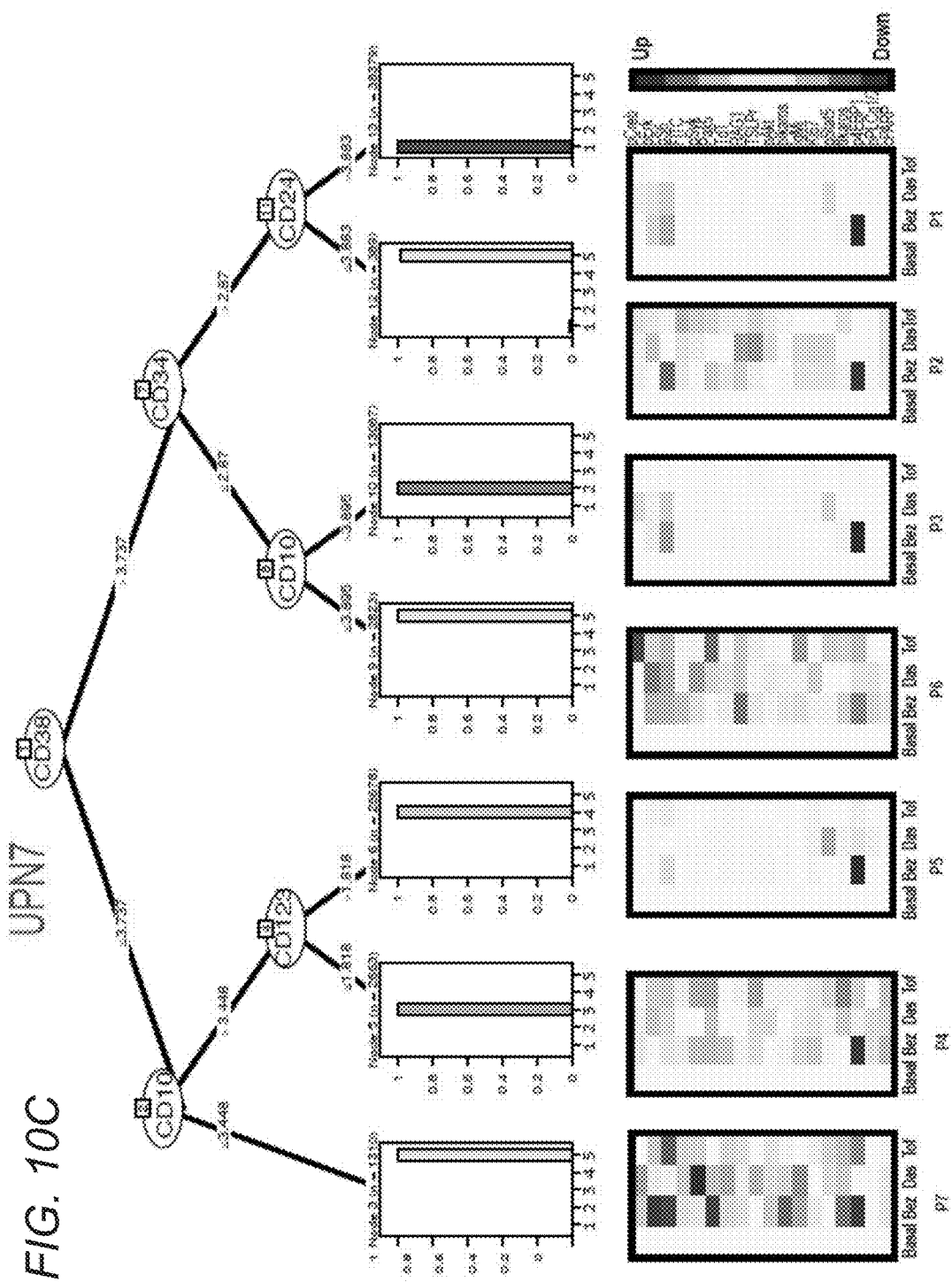
Figure 11:
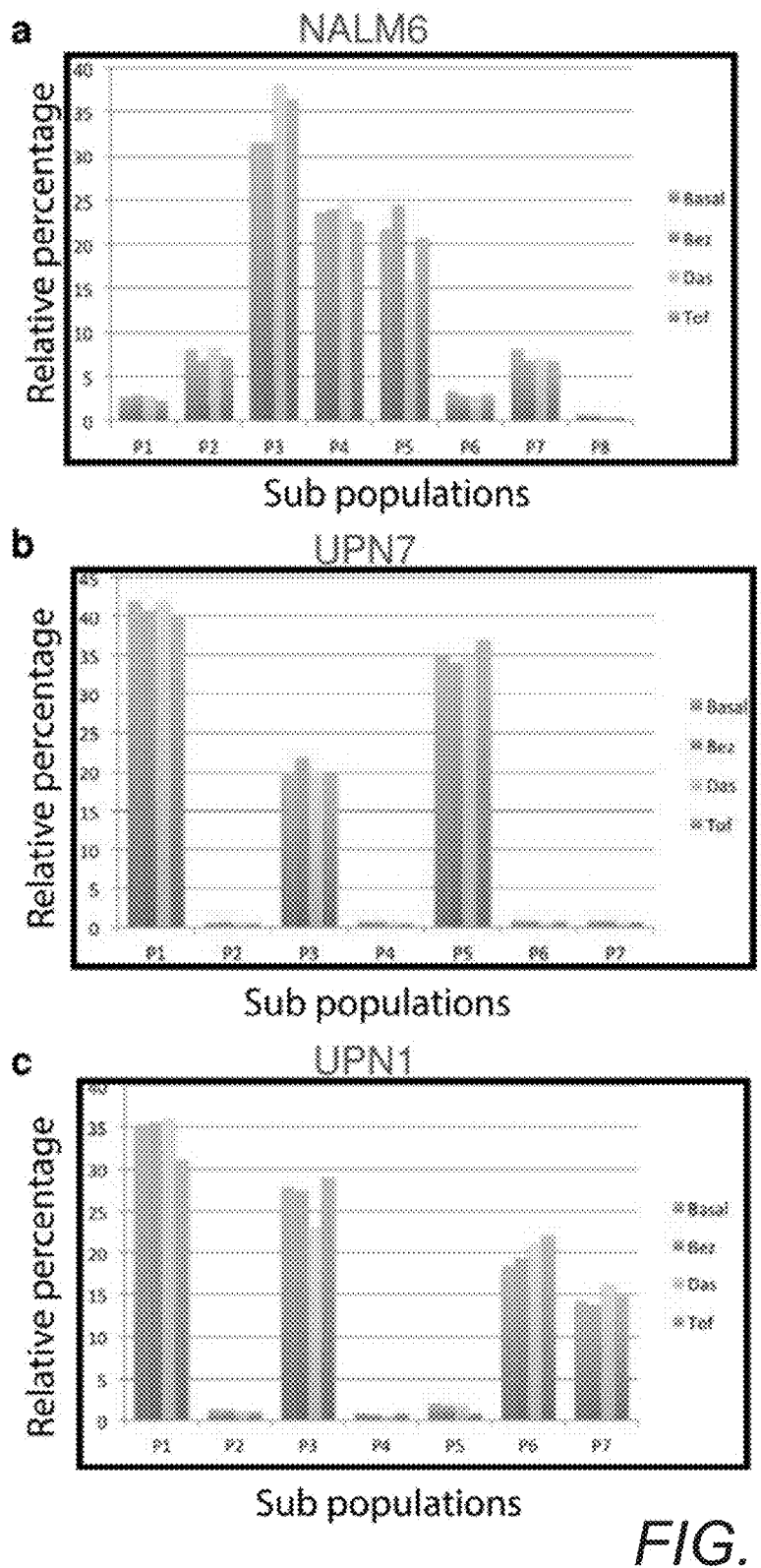
FIG. 11 illustrates bar plots comparing percentages of cells for major subpopulations from all inhibitors compared to basal populations (i.e. populations not subject to treatment).

The results are summarized in FIGS. 8B-8G The top row of FIG. 8B shows the 3D scatter plot of the distribution of NALM6, UPN7 and UPN1 cells condition on three markers color-coded by cPARP expression which typically differentiates between apoptotic and non-apoptotic cells. After manual gating there is still evidence of cPARP heterogeneity, in particular, the high cPARP cells corresponds to high pAkt for UPN7 and high IgMs, CD179a and CD10 for UPN1. This heterogeneity demonstrates that manually identifying the cells with cPARP high expression to improve the sensitivity of detecting signaling changes in different cell types is challenging in high dimensional datasets and further motivates the need for a more unsupervised automated approach. The bottom row of FIG. 8B shows the conditional distribution of the cells across all treatment conditions color coded here as blue (Basal), green(BEZ), pink(Das) and orange(Tof) under NALM6; and blue(Basal), black(Bez), orange(Das) and green(Tof) for UPN7 and UPN1 respectively. Assuming a minimum of 5-lineage subpopulations evidence from exploratory clustering with SPADE (Spanning Tree Progression of Density Normalized Events) (shown in FIG. 9), CCAST was used to identify and match seven cell subpopulations across the three inhibitors and basal conditions for each patient sample and the cell line (FIGS. 10A-10C). The relatively close percentages of cells for major subpopulations from all inhibitors compared to the basal populations (shown in FIG. 11) provide evidence of subpopulation stability before and after drug treatment. Comparing the subpopulations demonstrated strong down regulation effect of p4EBP1 by BEZ-235 across almost all subpopulations in the two patient samples (FIG. 8E) and all three samples (FIGS. 10A-10C). This phosphorylated oncogenic protein operates downstream of the PI3K/AKT/mTOR kinase signaling pathway and its downregulation signifies the inhibition of this particular pathway by BEZ-235. A greater number of effects to all three inhibitors are found in the smaller subpopulations, which demonstrates the necessity of identifying the subpopulations before computing the drug combinations. For both UPN1 and UPN7, using thirty different runs on down-sampled data of about 10,000 cells using the density dependent down sampling, the best drug combination predicted was BEZ+Das, based on drug-nested desired effects associated with decrease in fold change (shown in FIG. 8F, charts 802 and 804 in FIG. 8F). The corresponding most frequent drug-nested-effects models associated with these predictions are different for both patients (shown in FIG. 8F, models 806 and 808) in addition to the fact that BEZ and Das was the highest scoring combination for both patients.

The models were validated by performing an independent experiment treating the cells with the inhibitor combinations to determine if the optimal combination inhibits most of the targets. An independent analysis using CyTOF data on the two top drug combinations Das+Bez and Das+Tof for NALM6 and all three pairwise drug combinations under UPN7 and UPN1 is summarized in FIG. 8D. The nested effect model under NALM6 indicates the target effects of Das+Tof are nested within the target effects of Bez+Das while the target effects of Das+Tof and Bez+Tof are nested within the target effects of Bez+Das under UPN7, as predicted by the single drug model. Thus, both in a cell line model and in primary diagnostic leukemia cells, the analysis successfully identifies combinations of targeted inhibitors based on single drug treatment data, paving the way for a new approach to precision drug treatment.

Figure 8G:
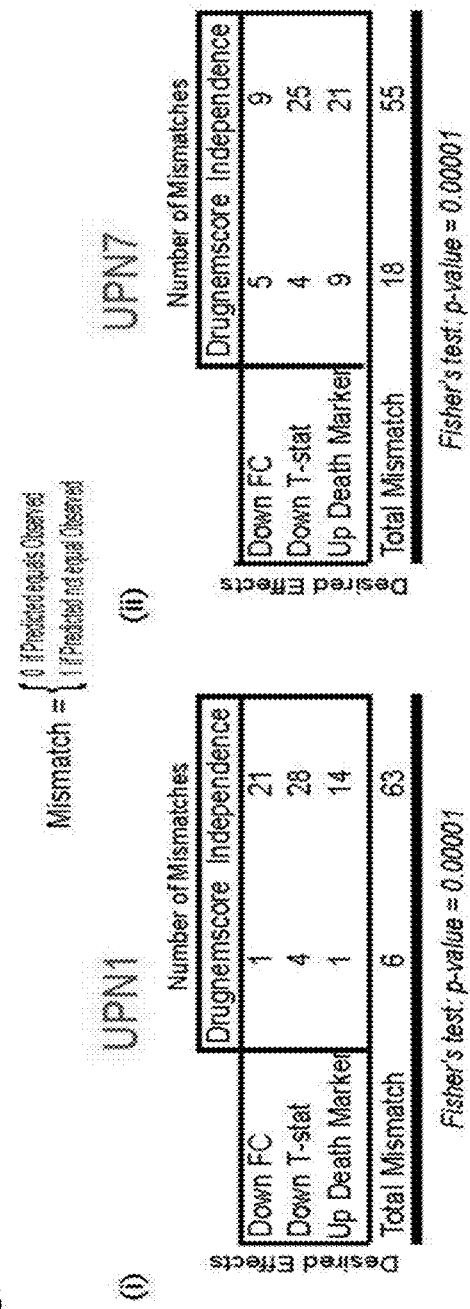

To validate the combination of BEZ+Das, all 2-drug combinations were analyzed by CyTOF using the same panel and then the combination with the maximum sum of the desired effects is compared with the best prediction resulting in a match (0) or mismatch (1), in the nested versus independence models. FIG. 8G shows that the nested model (Drugnemscore) outperforms the independence model (Independence) based on downregulated effects measured in terms of fold change (Down FC).

To account for the fact that not all markers will be associated with a particular desired phenotypic effect across different subpopulation of cells, two additional informative priors to estimate the probability of desired effects as weighted intracellular effects were used. The resulting desired effects can be derived from weighting: (i) the intracellular signaling effects with the probability odds of increasing downregulation derived from a T-statistics (Down T-statistic), and (ii) the intracellular signaling changes with probability of upregulation of death markers e.g. cPARP (Up Death Marker). The above desired effects can also be used to score drug combinations under the Independence model. FIG. 8G shows the contingency table for the number of mismatches between the predictions compared to the observed based on the above three desired effects subtypes (Desired Effects), the two scoring metrics) Drugnemscore and Independence), and 30 downsampled datasets of roughly 10,000 cells each, yielding a total of 180 (=3 Desired Effects×2 Scores×30 Downsampled Datasets) comparisons between the predictions and the observed. While the total number of mismatches across all desired effects subtypes is much smaller under Drugnemscore (6 for UPN1 and 18 for UPN7) compared to the Independence score (63 for UPN1 and 55 for UPN7). A Fisher's exact test based on Monte Carlo simulation robust to potential zero mismatches results in a significant 2-sided p-value (<0.05) for UPN1 (0.00001) and UPN7 (0.00001) showing that the distribution of mismatches under various desired effects is statistically different for both scoring metrics.

Figure 12A:
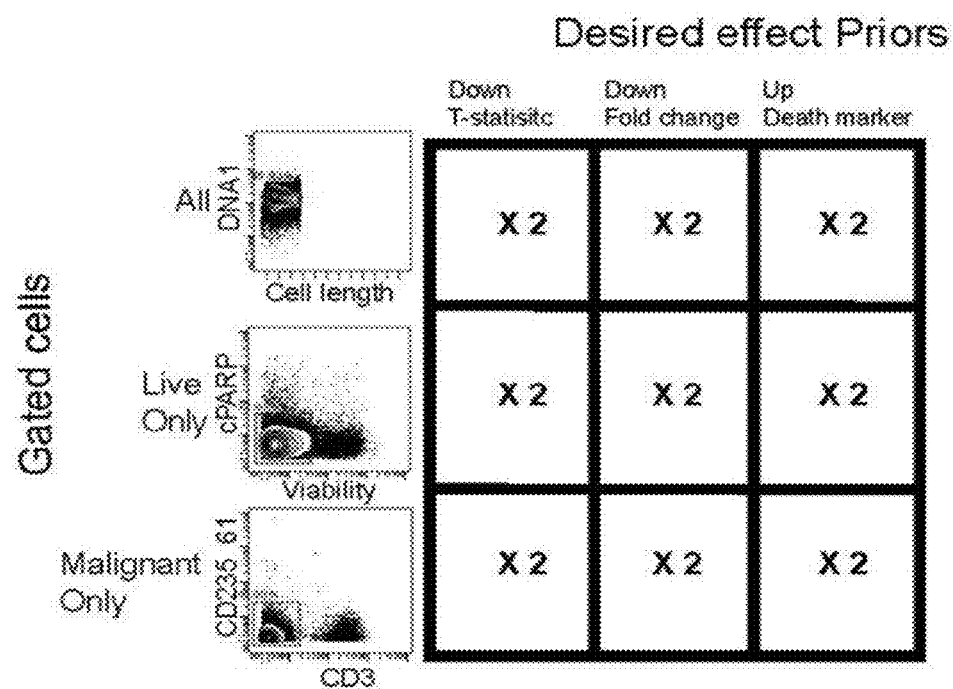
FIGS. 12A-12D illustrate a sensitivity analysis conducted on thirty patient samples.

Sensitivity analysis of the nested-effects model framework were conducted on thirty ALL patient samples: For each patient sample, variability were accounted for by applying the nested-effects model framework after three different gating strategies: (1) "All," denoting the entire sample including live and death cells, (2) "Live Only," denoting the manually gated live cells and (3) "Malignant-cells," denoting the manually gated malignant white blood cells (blasts), devoid for normal cells, such as T and myeloid cells. The gating strategies are summarized in FIG. 12A. Because each analysis was carried out on down-sampled data of about 10,000 cells per FCS file, the downsampling can be repeated twice to account for this variation. All three desired effects (Down FC, Down T-statistic, Up Death Marker) was carried out for each patient. In total, each patient was analyzed under 18 conditions (=3 Gating Strategies×3 Desired Effects×2 Downsampled Datasets).

Figure 12B:
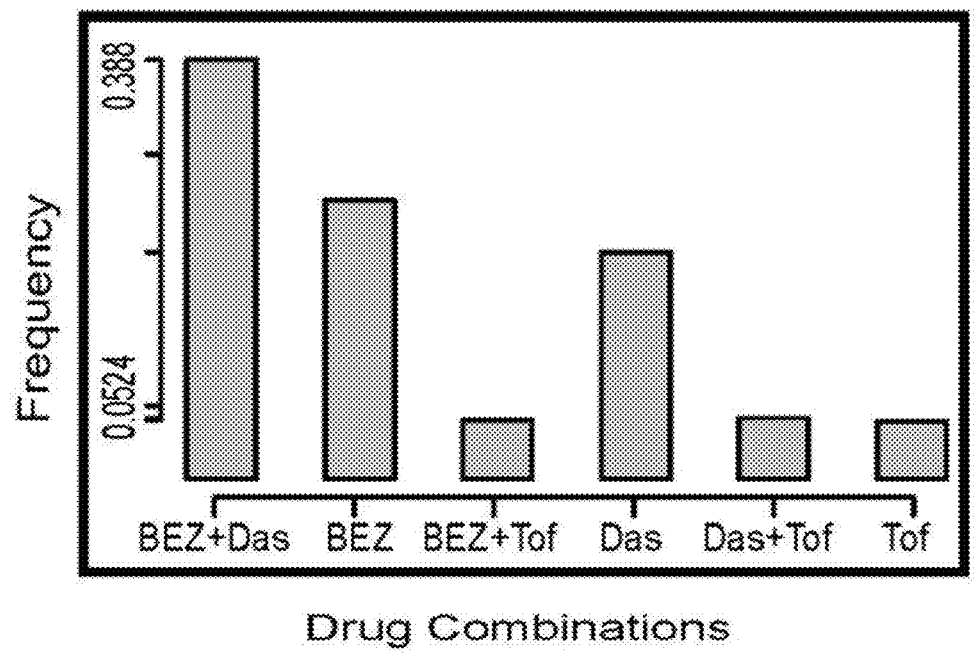
Figure 12C:
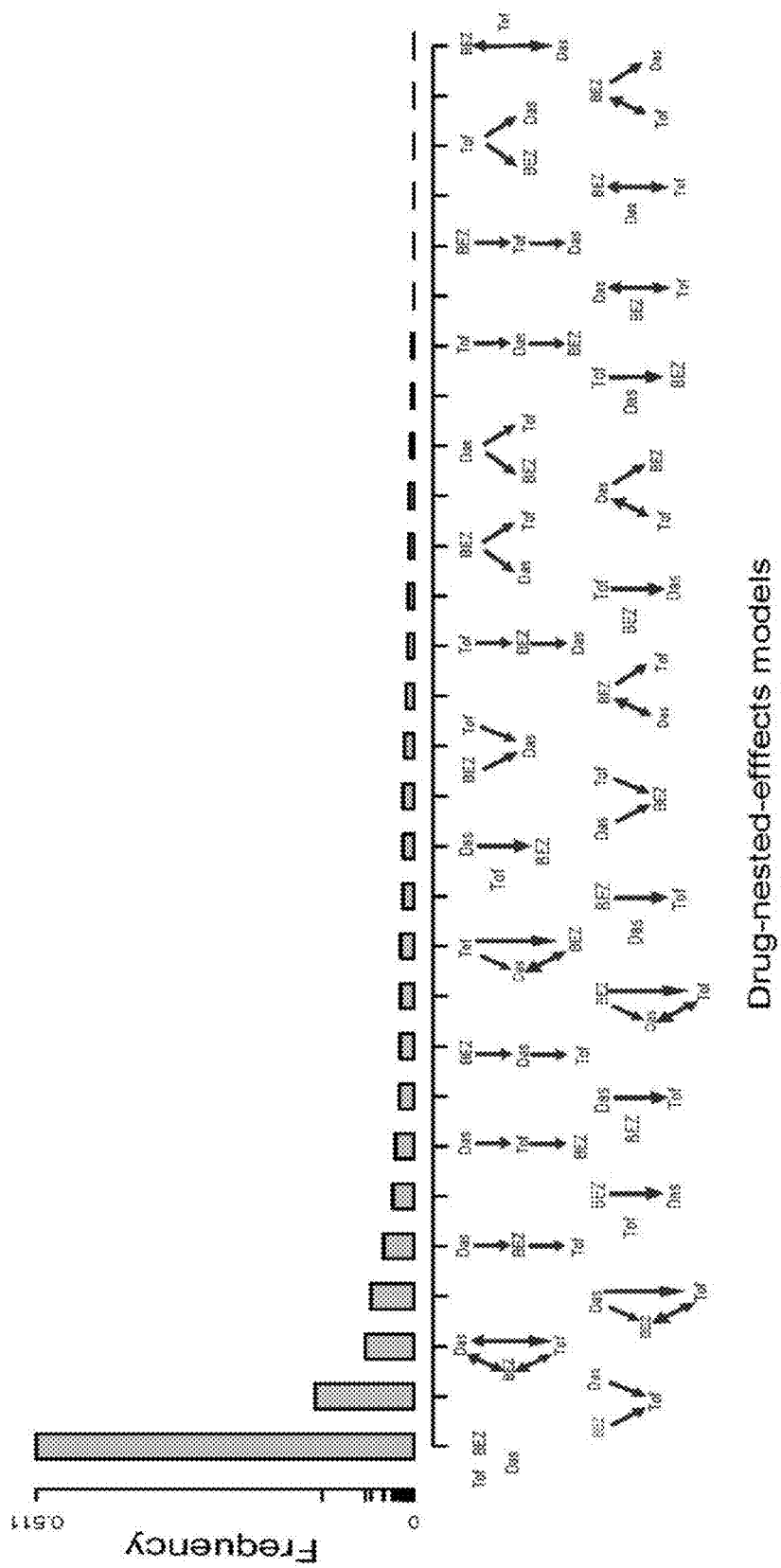
Figure 12D:
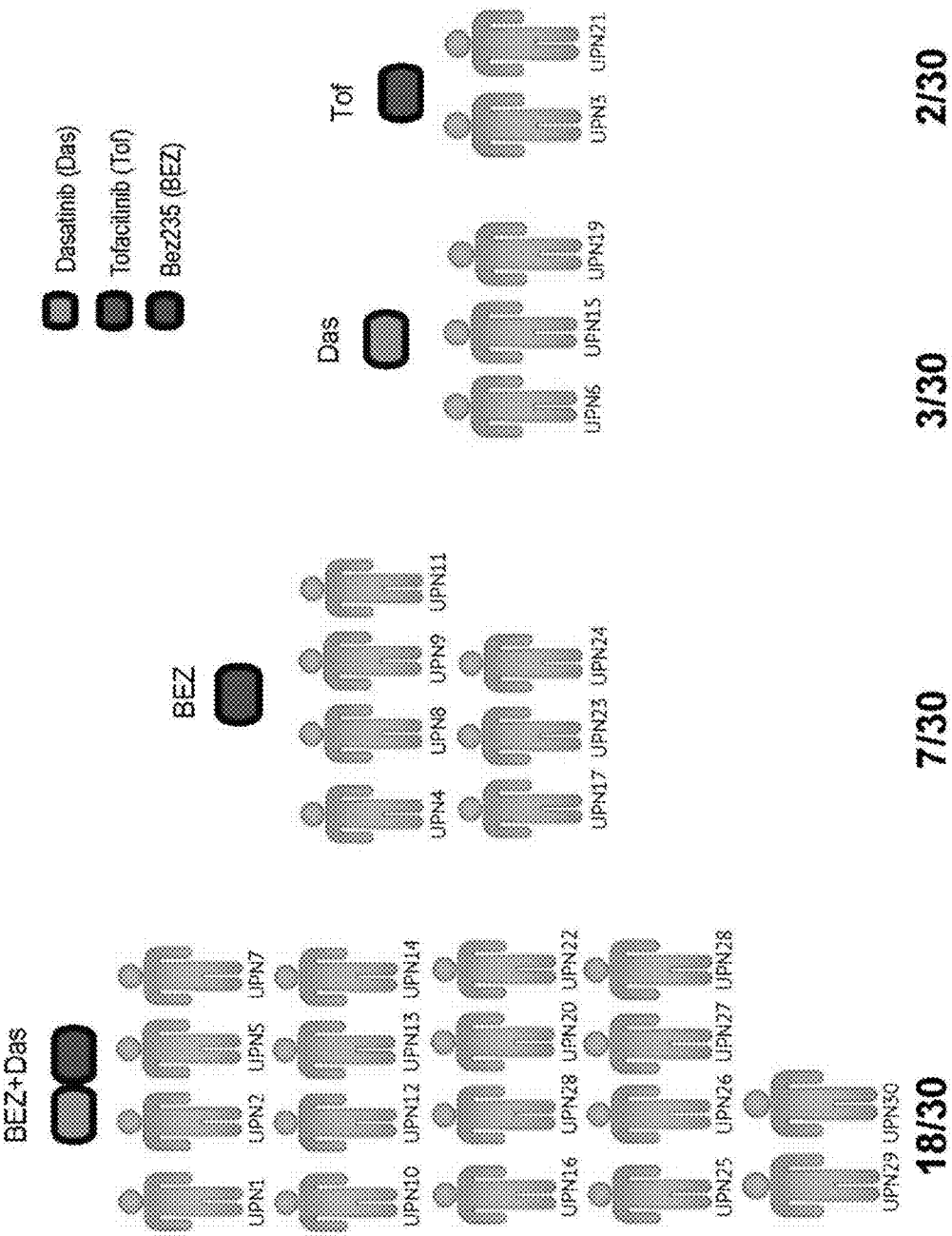

To determine if the BEZ+Das prediction by the nested-effects model framework can be generalized across all thirty patients, the top predictions are summarized into a bar plot distribution shown in FIG. 12B from a total of 540 predictions (30 patients×18 conditions/patient). Although BEZ+Das had a 37% chance of being selected as the best drug combination, the nested-effects model framework selected BEZ alone and Das alone as the optimal therapy for about 30% of the patients (FIG. 12D; see UPN4, UPN8, UPN9, etc.). FIG. 12C provides the summary distribution of the network models that underlie the scoring distributions. The top two networks explain why BEZ+Das had the highest score. In summary, this analysis suggests while there may be a single dominant 2-drug strategy (BEZ+Das) for the vast majority of ALL patients, it may not be optimal for all patients.

The effect of BEZ+Das was tested by performing two independent viability analysis assays on three independent ALL related cell lines, treating the cells with both the single inhibitors and combination of BEZ+Das and observing the cell growth over a period of at least 72 hours. The cell lines tested were: NALM6 cell line which is a precursor (pre)-B human cell line derived from an adult ALL relapsed patient and is highly efficient for gene targeting by homologous recombination; NALM1 cell line, a non-T, non-B human leukemia cell line (NALM-1) and SUP-B15 cell line derived from a Ph+ALL child. The biggest decrease in cell viability can be observed over time for all cell lines using both drugs compared to the single drug conditions with almost all the cells killed in the SUP-B15 cell line after 72 hours. FIG. 13A shows the survival curves for all three cell lines exposed to both single and drug combinations at optimal dose concentrations over a period of at least 72 hours. The figures are derived from average survival values of each cell line treatment condition. BEZ+Das seem to consistently achieve the most cell kill after 72 hours compared to the single drugs closely followed by Das, which seems to synergize with BEZ to increase cell death. Standard measure of drug effectiveness known as the Combination Index (CI) were used to investigate the presence of a synergistic (CI<1) or additive (CI=1) BEZ+Das effect. Under bliss independence for fractional cell kill, FIG. 13B illustrates and quantifies the synergistic effect of BEZ+Das across all three cell lines. The synergistic effect is strongest in the NALM1 cell line with a CI value of 0.86. In summary, the results from both the cell line models and primary diagnostic leukemia samples show that the nested-effects model framework can identify optimal combinations of targeted inhibitors based on single-cell, single drug treatment, and signaling perturbation data paving the way for a new approach to precision drug treatment.

Figure 14A:
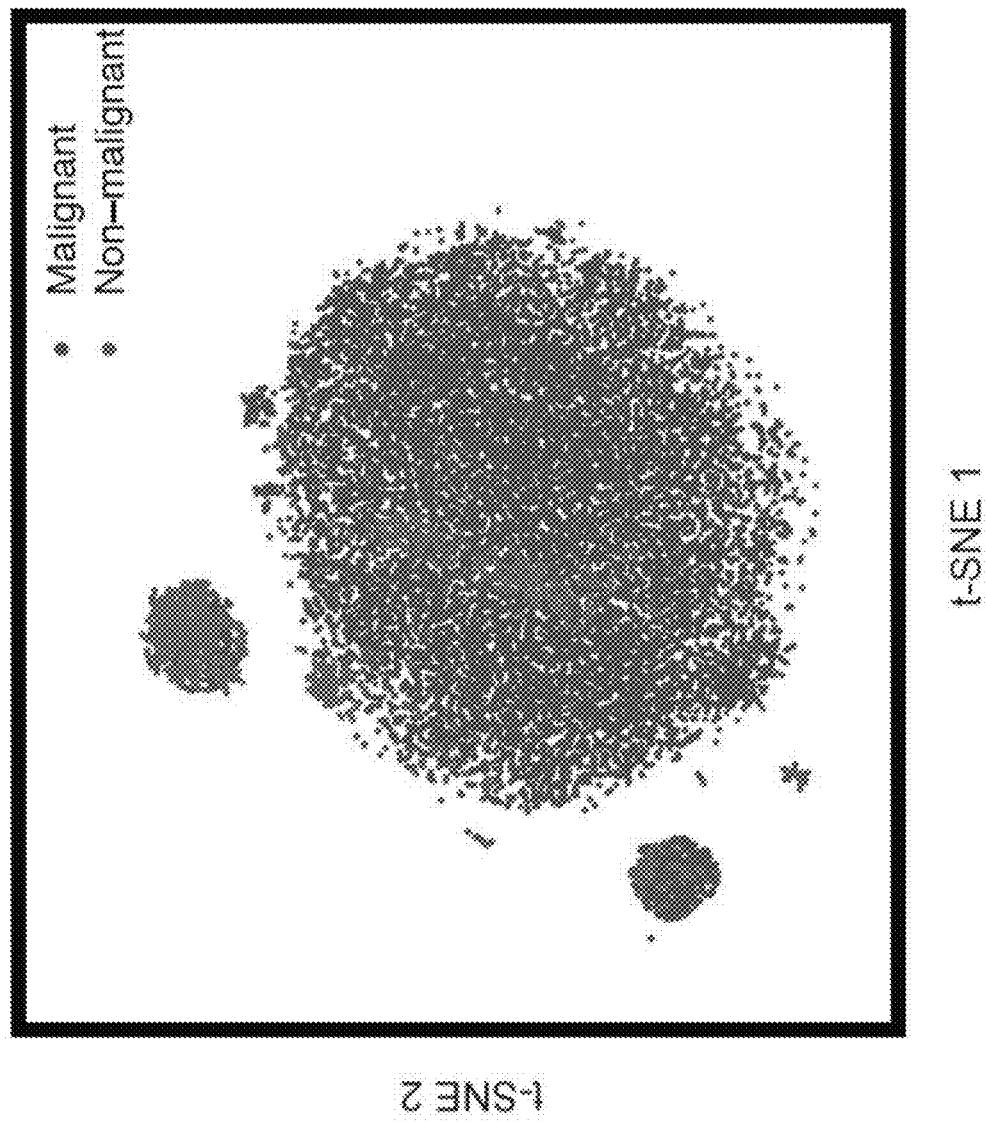

Methods in accordance with many embodiments of the invention can be optimized for different responses in different cell types. In many embodiments, the optimization algorithm can enable the possibility for optimizing drug combinations based on desired intracellular effects in malignant cells and possibly different desired intracellular effects in nonmalignant cells. Drug regimens with the potential to increase death signaling in the malignant subpopulation can be optimized while at the same increase survival signaling in the non-malignant cells. Since the desired effects can be measured in terms of probability, assuming $w_{ij|k}$ represents the prior probability of a desired effect associated with intracellular signaling marker $M_i$ under drug $S_j$ in subpopulations $k_1$ and $k_2$ for both malignant and non-malignant subpopulations, respectively, then the desired effect probability associated with each marker in the non-malignant subpopulation becomes $w_{ij|k}^c$ where $w_{ij|k}^c$ represents the probability of the complimentary or opposite effect. For example using the "Down FC" priors can optimize the combinations using down regulated effects for malignant cells and upregulation for non-malignant cells. FIGS. 14A-14D illustrate this concept for ALL patient UPN1. FIG. 14A shows the highlighted t-SNE plot for both malignant and non-malignant gated cells. FIG. 14B shows the drug-nested-effects model (top) and heatmap (below) under assuming the same desired effects for both cell types. FIG. 14C shows the drug-nested-effects model (top) and heatmap (below) desired effects associated upregulation in the non-malignant cells. The results in FIGS. 14B and 14C can differ based on whether or not the different cell types were weighted differently. Using the results from FIG. 14C, FIG. 14D shows the ranking distribution with Das, Bez+Das and Das+Tof as potential optimal regimens for the patient. Note that the results in FIGS. 14A-14D differ from prior results on UPN1 because this analysis did not account for the intratumoral heterogeneity in the malignant cells. These results only illustrate the extension of nested-effects model framework to nonmalignant cells.

Figure 15:
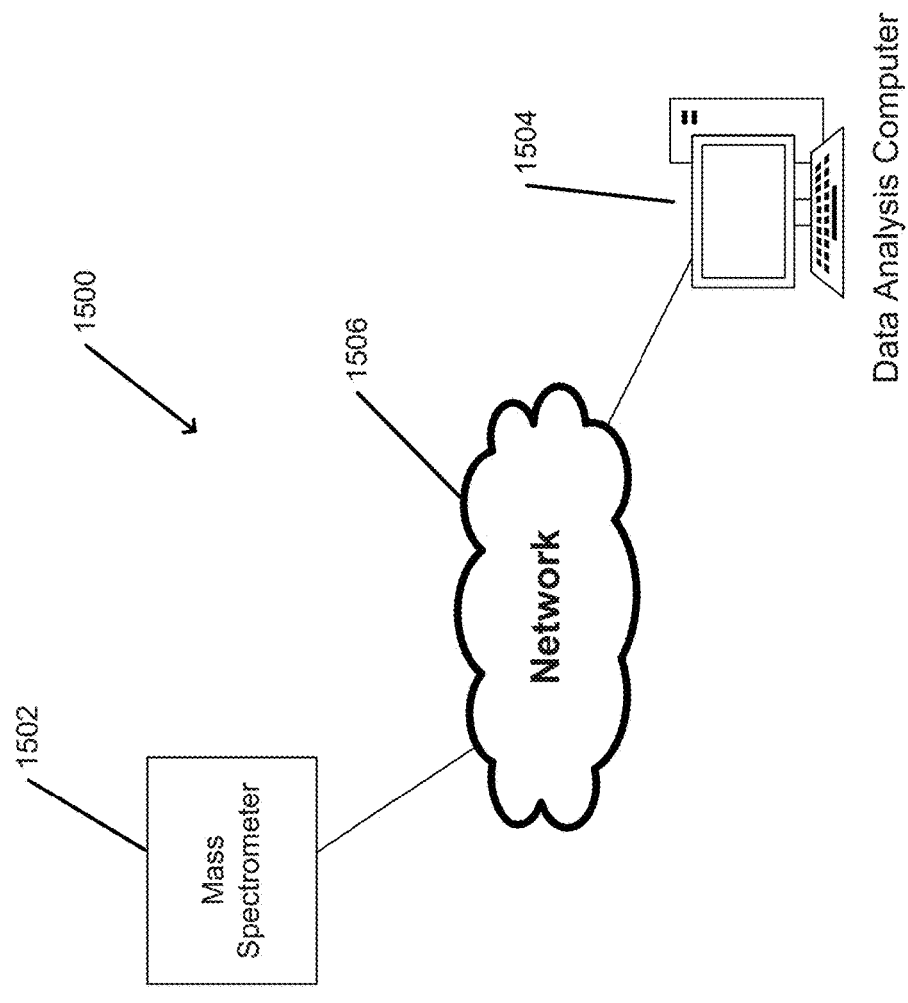
FIG. 15 is a system diagram of a data analysis system for acquiring and analyzing mass spectrometry data in accordance with an embodiment of the invention.

Embodiments of the invention, including those described above, can be performed on a variety of systems. The system can be a simple computing device capable of receiving and analyzing mass spectrometry data. A data analysis system in accordance with an embodiment of the invention is illustrated in FIG. 1. The data analysis 1500 includes a mass spectrometer 1502. In the illustrated embodiment, the mass spectrometer 1502 is configured to provide data to a data analysis computer 1504 via a network 1506. In many embodiments, the data analysis computer is a personal computer, server, and/or any other computing device with the storage capacity and processing power to analyze the data output by the mass spectrometer. The analysis computing device can include a processor, memory, and/or a storage system containing an application that includes machine readable instructions that configures the computer to perform nested-effects-modeling analysis on a mass spectrometry data set. Although a specific data analysis system is illustrated in FIG. 15, any of a variety of data analysis systems can be utilized to analyze mass spectrometry data using nested-effects modeling in accordance with embodiments of the invention.

Although specific methods of identifying optimal drug combinations are discussed above, many different methods can be implemented in accordance with many various embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for optimizing stimulus combinations for therapy, the method comprising:
   receiving a cell sample;
   treating the cell sample with a plurality of stimuli by treating a different portion of the cell sample with one of the plurality of stimuli for each of the plurality of stimuli;
   labeling the treated cell sample with a plurality of metal-conjugated antibodies, wherein the plurality of metal-conjugated antibodies corresponds with a set of markers;
   analyzing the labeled cell sample using a mass spectrometer;
   obtaining mass spectrometry data from the mass spectrometer, wherein the mass spectrometry data describe perturbation responses;
   identifying subpopulations within the cell sample using the mass spectrometry data using a computing device;
   computing stimulus effects using the mass spectrometry data using the computing device;
   generating a nested-effects model using the mass spectrometry data and the stimulus effects using the computing device, wherein the nested-effects model describes the relationships between the plurality of stimuli and the set of markers across the subpopulations;
   scoring stimulus combinations using the nested-effects model using the computing device, wherein the stimulus combinations are combinations made from the plurality of stimuli; and
   outputting a list of ranked stimulus combinations based on the scored stimulus combinations.

2. The method of claim 1, wherein the nested-effects model is represented as a directed graph.

3. The method of claim 1, wherein the stimulus effects are computed using Bayesian linear models.

4. The method of claim 1, wherein the set of markers comprises at least one lineage marker and at least one intracellular signaling marker, wherein the subpopulations are identified using the at least one lineage marker.

5. The method of claim 4, wherein the set of markers further comprises at least one death marker, wherein the method further comprises removing apoptotic cell data from the mass spectrometry data for cells that are committed to apoptosis using the at least one death marker.

6. The method of claim 5, wherein the apoptotic cell data are removed and the subpopulations are identified using a decision tree.

7. The method of claim 1, wherein the stimulus combinations are scored based on minimizing the amount of stimuli in the stimulus combination while maximizing a desired effect.

8. The method of claim 1, wherein scoring the stimulus combinations take into account side effects of the stimulus combinations.

9. The method of claim 1, the stimulus effects are computed with weightings using prior knowledge.

10. The method of claim 1, wherein the subpopulations are identified through manual gating.

* * * * *